US012404554B2

(12) United States Patent
Chiesi et al.

(10) Patent No.: US 12,404,554 B2
(45) Date of Patent: Sep. 2, 2025

(54) METHODS AND KITS RELATING TO THE CAPTURE OF CA-IX POSITIVE EXOSOMES

(71) Applicant: EXOSOMICS S.P.A., Siena (IT)

(72) Inventors: Antonio Chiesi, Siena (IT); Natasa Zarovni, Siena (IT); Davide Zocco, Siena (IT)

(73) Assignee: EXOSOMICS S.P.A., Siena (IT)

( * ) Notice: Subject to any disclaimer, the term of this patent is extended or adjusted under 35 U.S.C. 154(b) by 126 days.

(21) Appl. No.: 16/623,360

(22) PCT Filed: Jun. 21, 2018

(86) PCT No.: PCT/EP2018/066604
§ 371 (c)(1),
(2) Date: Dec. 16, 2019

(87) PCT Pub. No.: WO2018/234463
PCT Pub. Date: Dec. 27, 2018

(65) Prior Publication Data
US 2020/0291482 A1 Sep. 17, 2020

(30) Foreign Application Priority Data
Jun. 21, 2017 (EP) ..................................... 17177190

(51) Int. Cl.
*C12Q 1/6886* (2018.01)
*G01N 33/543* (2006.01)

(52) U.S. Cl.
CPC ..... *C12Q 1/6886* (2013.01); *G01N 33/54306* (2013.01); *C12Q 2600/156* (2013.01)

(58) Field of Classification Search
CPC .......................... C12Q 1/6886; C12Q 2563/161
See application file for complete search history.

(56) References Cited

FOREIGN PATENT DOCUMENTS

| WO | WO-2011139375 A1 | * | 11/2011 | ............. C07K 16/40 |
|----|---|---|---|---|
| WO | 2012115885 A1 | | 8/2012 | |
| WO | 2015153732 A2 | | 10/2015 | |

OTHER PUBLICATIONS

Dorai, T. Glycobiology Insights 1:3-12. (Year: 2009).*
International Search Report issued by the European Patent Office for corresponding Application No. PCT/EP2018/066604, dated Aug. 15, 2018, Rijswijk, Netherlands.
Chamie, et al.; "Carbonic anhydrase-IX score is a novel biomarker that predicts recurrence and survival for high-risk, nonmetastatic renal cell carcinoma: Data from the phase III ARISER clinical trial", Urologic Oncology: Seminars and Original Investigations, May 2015, vol. 33, Issue 5, pp. 204.e25-204.e33, Elsevier Inc.
Pastorek, et al., "Hypoxia-induced carbonic anhydrase IX as a target for cancer therapy: From biology to clinical use", Seminars in Cancer Biology, 2014, vol. 31, pp. 52-64, Elsevier Ltd.

(Continued)

*Primary Examiner* — Diana B Johannsen
(74) *Attorney, Agent, or Firm* — Bradley Arant Boult Cummings LLP; Henry B. Ward, III

(57) ABSTRACT

Methods and kits for isolating tumour-derived exosomes by immunocapture with an anti CA-IX antibody, quantifying tumour-related nucleic acid sequences from the isolated exosomes and determining in vitro the presence of a tumour in a subject are provided.

6 Claims, 22 Drawing Sheets

Specification includes a Sequence Listing.

A)

B)

C)

(56) References Cited

OTHER PUBLICATIONS

Takacova, et al., "Carbonic anhydrase IX is a clinically significant tissue and serum biomarker associated with renal cell carcinoma", Oncology Letters, 2013, vol. 5, Issue 1, pp. 191-197, Spandidos Publications.

Davies, H., et al., "Mutation of the BRAF gene in human cancer", Letters to Nature, Jun. 27, 2002, vol. 417, pp. 949-954, Nature Publishing Group.

Corcoran, et al., "BRAF Gene Amplification Can Promote Acquired Resistance to MEK Inhibitors In Cancer Cells Harboring The BRAF V600E Mutation", Science Signaling, 2010, vol. 3, Issue 149, pp. 1-20, American Association for the Advancement of Science.

Perincheri, et al. "KRAS Mutation testing in clinical practice", Expert Review of Molecular Diagnostics, 2014, vol. 15, Issue 3, pp. 375-384, Informa UK Ltd.

Cercek, et al., "Clinical Features and Outcomes of Patients with Colorectal Cancers Harboring NRAS Mutations", Clinical Cancer Research, Aug. 15, 2017, vol. 23, Issue 16, pp. 4753-4760, American Association for Cancer Research.

Mandalà, et al., "Nras in melanoma: Targeting the undruggable target", Critical Reviews in Oncology/Hematology, 2014, vol. 92, Issue 2, pp. 107-122, Elsevier Ireland Ltd.

Passaro, et al., "Targeting EGFR T790M mutation in NSCLC: From biology to evaluation and treatment", Pharmacological Research, 2017, vol. 117, pp. 406-415, Elsevier Ltd.

Fang, et al., "EGFR mutations as a prognostic and predictive marker in non-small-cell lung cancer", Drug Design, Development and Therapy, 2014, vol. 8, pp. 1595-1611, Dove Medical Press Limited.

Gabay, et al., "MYC Activation Is a Hallmark of Cancer Initiation and Maintenance", Cold Spring Harbor Perspective in Medicine, 2014, vol. 4(6), 4:a014241, Cold Spring Harbor Laboratory Press.

Balaj, et al., "Tumour microvesicles contain retrotransposon elements and amplified oncogene sequences", Nature Communications, Feb. 2011, 2:180, Macmillan Publishers Limited.

Romanel, et al., "Plasma AR and abiraterone-resistant prostate cancer", Science Translational Medicine, Nov. 4, 2015, vol. 7, Issue 312, pp. 312re10, American Association for the Advancement of Science.

Antonarakis, et al., "AR-V7 and Resistance to Enzalutamide and Abiraterone in Prostate Cancer", The New England Journal of Medicine, Sep. 11, 2014, vol. 371, No. 11, pp. 1028-1038, Massachusetts Medical Society.

Cheadle, et al., "Analysis of Microarray Data Using Z Score Transformation", The Journal of Molecular Diagnostics, May 2003, vol. 5, Issue 2, pp. 73-81, American Society for Investigative Pathology and the Association for Molecular Pathology, Elsevier Inc.

Tauro, et al., Two Distinct Populations of Exosomes Are Released from LIM1863 Colon Carcinoma Cell-derived Organoids, Molecular & Cellular Proteomics, Dec. 10, 2012, vol. 12, No. 3, pp. 587-598, The American Society for Biochemistry and Molecular Biology, Inc.

Zhang, et al., "Exosomes derived from IL-12-anchored renal cancer cells increase induction of specific antitumor response in vitro: A novel vaccine for renal cell carcinoma", International Journal Of Oncology, 2009, vol. 36, Issue 1, pp. 133-140, Spandidos Publications.

Abols, et al., "Carbonic anhydrase IX as the marker of the hypoxia induced extracellular vesicle secretion" (abstract p0368), United European Gastroenterology Journal, 2016, vol. 4, No. Supplement 5, p. A284.

Dorai, et al., "366 carbonic anhydrase IX shedding through exosomes in renal carcinoma cells", The Journal of Urology, 2010, vol. 183, No. 4, p. e145.

Kalra, et al., "Comparative proteomics evaluation of plasma exosome isolation techniques and assessment of the stability of exosomes in normal human blood plasma", Proteomics, 2013, vol. 13, No. 22, pp. 3354-3364, Wiley.

Written Opinion issued by the European Patent Office for corresponding Application No. PCT/EP2018/066604, dated Aug. 15, 2018, Rijswijk, Netherlands.

International Preliminary Report on Patentability issued by the European Patent Office for corresponding Application No. PCT/EP2018/066604, dated Dec. 24, 2019.

\* cited by examiner

A)

B)

C)

A)

B)

SEQUENCE LISTING

```
<160> NUMBER OF SEQ ID NOS: 32

<210> SEQ ID NO 1
<211> LENGTH: 25
<212> TYPE: DNA
<213> ORGANISM: artificial sequence
<220> FEATURE:
<223> OTHER INFORMATION: BRAF preamp primer

<400> SEQUENCE: 1
taggtgattt tggtctagct acagt                                              25

<210> SEQ ID NO 2
<211> LENGTH: 24
<212> TYPE: DNA
<213> ORGANISM: artificial sequence
<220> FEATURE:
<223> OTHER INFORMATION: BRAF preamp primer

<400> SEQUENCE: 2
ttaatcagtg gaaaaatagc ctca                                               24

<210> SEQ ID NO 3
<211> LENGTH: 25
<212> TYPE: DNA
<213> ORGANISM: artificial sequence
<220> FEATURE:
<223> OTHER INFORMATION: BRAF preamp primer

<400> SEQUENCE: 3
taggtgattt tggtctagct acaga                                              25

<210> SEQ ID NO 4
<211> LENGTH: 24
<212> TYPE: DNA
<213> ORGANISM: artificial sequence
<220> FEATURE:
```

```
<223> OTHER INFORMATION: BRAF preamp primer

<400> SEQUENCE: 4
ttaatcagtg gaaaaatagc ctca                                              24

<210> SEQ ID NO 5
<211> LENGTH: 19
<212> TYPE: DNA
<213> ORGANISM: artificial sequence
<220> FEATURE:
<223> OTHER INFORMATION: KRAS preamp primer

<400> SEQUENCE: 5
ggtagttgga gctggtggc                                                    19

<210> SEQ ID NO 6
<211> LENGTH: 26
<212> TYPE: DNA
<213> ORGANISM: artificial sequence
<220> FEATURE:
<223> OTHER INFORMATION: KRAS preamp primer

<400> SEQUENCE: 6
tgattctgaa ttagctgtat cgtcaa                                            26

<210> SEQ ID NO 7
<211> LENGTH: 25
<212> TYPE: DNA
<213> ORGANISM: artificial sequence
<220> FEATURE:
<223> OTHER INFORMATION: BRAF qPCR primer or probe

<400> SEQUENCE: 7
taggtgattt tggtctagct acagt                                             25

<210> SEQ ID NO 8
<211> LENGTH: 24
<212> TYPE: DNA
<213> ORGANISM: artificial sequence
<220> FEATURE:
<223> OTHER INFORMATION: BRAF qPCR primer or probe

<400> SEQUENCE: 8
ttaatcagtg gaaaaatagc ctca                                              24

<210> SEQ ID NO 9
<211> LENGTH: 25
<212> TYPE: DNA
<213> ORGANISM: artificial sequence
<220> FEATURE:
<223> OTHER INFORMATION: BRAF qPCR primer or probe

<400> SEQUENCE: 9
taggtgattt tggtctagct acaga                                             25

<210> SEQ ID NO 10
<211> LENGTH: 24
<212> TYPE: DNA
<213> ORGANISM: artificial sequence
<220> FEATURE:
<223> OTHER INFORMATION: BRAF qPCR primer or probe

<400> SEQUENCE: 10
ttaatcagtg gaaaaatagc ctca                                              24
```

```
<210> SEQ ID NO 11
<211> LENGTH: 38
<212> TYPE: DNA
<213> ORGANISM: artificial sequence
<220> FEATURE:
<223> OTHER INFORMATION: BRAF qPCR primer or probe

<400> SEQUENCE: 11
ccgaagggga tccagacaac tgttcaaact gccttcgg                             38

<210> SEQ ID NO 12
<211> LENGTH: 19
<212> TYPE: DNA
<213> ORGANISM: artificial sequence
<220> FEATURE:
<223> OTHER INFORMATION: KRAS qPCR primer or probe

<400> SEQUENCE: 12
ggtagttgga gctggtggc                                                  19

<210> SEQ ID NO 13
<211> LENGTH: 26
<212> TYPE: DNA
<213> ORGANISM: artificial sequence
<220> FEATURE:
<223> OTHER INFORMATION: KRAS qPCR primer or probe

<400> SEQUENCE: 13
tgattctgaa ttagctgtat cgtcaa                                          26

<210> SEQ ID NO 14
<211> LENGTH: 15
<212> TYPE: DNA
<213> ORGANISM: artificial sequence
<220> FEATURE:
<223> OTHER INFORMATION: KRAS qPCR primer or probe

<400> SEQUENCE: 14
cactcttgcc tacgc                                                      15

<210> SEQ ID NO 15
<211> LENGTH: 23
<212> TYPE: DNA
<213> ORGANISM: artificial sequence
<220> FEATURE:
<223> OTHER INFORMATION: EGFR qPCR primer or probe

<400> SEQUENCE: 15
gcagcatgtc aagatcacag att                                             23

<210> SEQ ID NO 16
<211> LENGTH: 25
<212> TYPE: DNA
<213> ORGANISM: artificial sequence
<220> FEATURE:
<223> OTHER INFORMATION: EGFR qPCR primer or probe

<400> SEQUENCE: 16
cctccttctg catggtattc tttct                                           25

<210> SEQ ID NO 17
<211> LENGTH: 16
<212> TYPE: DNA
<213> ORGANISM: artificial sequence
<220> FEATURE:
<223> OTHER INFORMATION: EGFR qPCR primer or probe
```

```
<400> SEQUENCE: 17
agtttggcca gcccaa                                                    16

<210> SEQ ID NO 18
<211> LENGTH: 22
<212> TYPE: DNA
<213> ORGANISM: artificial sequence
<220> FEATURE:
<223> OTHER INFORMATION: cMyc qPCR primer or probe

<400> SEQUENCE: 18
ccctccactc ggaaggacta tc                                             22

<210> SEQ ID NO 19
<211> LENGTH: 22
<212> TYPE: DNA
<213> ORGANISM: artificial sequence
<220> FEATURE:
<223> OTHER INFORMATION: cMyc qPCR primer or probe

<400> SEQUENCE: 19
aggactctga cactgtccaa ct                                             22

<210> SEQ ID NO 20
<211> LENGTH: 18
<212> TYPE: DNA
<213> ORGANISM: artificial sequence
<220> FEATURE:
<223> OTHER INFORMATION: cMyc qPCR primer or probe

<400> SEQUENCE: 20
tgaccctctt ggcagcag                                                  18

<210> SEQ ID NO 21
<211> LENGTH: 23
<212> TYPE: DNA
<213> ORGANISM: artificial sequence
<220> FEATURE:
<223> OTHER INFORMATION: LINE qPCR primer or probe

<400> SEQUENCE: 21
tcaacaagaa gagctaacta tcc                                            23

<210> SEQ ID NO 22
<211> LENGTH: 22
<212> TYPE: DNA
<213> ORGANISM: artificial sequence
<220> FEATURE:
<223> OTHER INFORMATION: LINE qPCR primer or probe

<400> SEQUENCE: 22
ttgtaggtca ctcaggactt gc                                             22

<210> SEQ ID NO 23
<211> LENGTH: 29
<212> TYPE: DNA
<213> ORGANISM: artificial sequence
<220> FEATURE:
<223> OTHER INFORMATION: LINE qPCR primer or probe

<400> SEQUENCE: 23
tgcacccaat acaggagcac ccagattca                                      29

<210> SEQ ID NO 24
<211> LENGTH: 24
```

```
<212> TYPE: DNA
<213> ORGANISM: artificial sequence
<220> FEATURE:
<223> OTHER INFORMATION: HERV-W qPCR primer or probe

<400> SEQUENCE: 24
cttccagaat tgaagctgta aagc                                    24

<210> SEQ ID NO 25
<211> LENGTH: 22
<212> TYPE: DNA
<213> ORGANISM: artificial sequence
<220> FEATURE:
<223> OTHER INFORMATION: HERV-W qPCR primer or probe

<400> SEQUENCE: 25
gggttgtgca gttgagattt cc                                      22

<210> SEQ ID NO 26
<211> LENGTH: 26
<212> TYPE: DNA
<213> ORGANISM: artificial sequence
<220> FEATURE:
<223> OTHER INFORMATION: HERV-W qPCR primer or probe

<400> SEQUENCE: 26
ttcttcaaat ggagccccag atgcag                                  26

<210> SEQ ID NO 27
<211> LENGTH: 21
<212> TYPE: DNA
<213> ORGANISM: artificial sequence
<220> FEATURE:
<223> OTHER INFORMATION: AR-WT FW primer

<400> SEQUENCE: 27
cagcctattg cgagagagct g                                       21

<210> SEQ ID NO 28
<211> LENGTH: 21
<212> TYPE: DNA
<213> ORGANISM: artificial sequence
<220> FEATURE:
<223> OTHER INFORMATION: AR-WT RW primer

<400> SEQUENCE: 28
gaaaggatct tgggcacttg c                                       21

<210> SEQ ID NO 29
<211> LENGTH: 18
<212> TYPE: DNA
<213> ORGANISM: artificial sequence
<220> FEATURE:
<223> OTHER INFORMATION: AR-WT probe

<400> SEQUENCE: 29
agttcacttt tgacctgc                                           18

<210> SEQ ID NO 30
<211> LENGTH: 26
<212> TYPE: DNA
<213> ORGANISM: artificial sequence
<220> FEATURE:
<223> OTHER INFORMATION: AR-V7 FW primer

<400> SEQUENCE: 30
```

```
ccatcttgtc gtcttcggaa atgtta                               26

<210> SEQ ID NO 31
<211> LENGTH: 26
<212> TYPE: DNA
<213> ORGANISM: artificial sequence
<220> FEATURE:
<223> OTHER INFORMATION: AR-V7 RW primer

<400> SEQUENCE: 31
tttgaatgag gcaagtcagc ctttct                               26

<210> SEQ ID NO 32
<211> LENGTH: 17
<212> TYPE: DNA
<213> ORGANISM: artificial sequence
<220> FEATURE:
<223> OTHER INFORMATION: AR-V7 probe

<400> SEQUENCE: 32
aagcagggat gactctg                                         17
```

METHODS AND KITS RELATING TO THE CAPTURE OF CA-IX POSITIVE EXOSOMES

CROSS-REFERENCE TO RELATED APPLICATIONS

This application is filed under the provisions of 35 U.S.C. 371 as national stage of International Patent Application No. PCT/EP2018/066604, filed on Jun. 21, 2018 entitled "METHODS AND KITS RELATING TO THE CAPTURE OF CA-IX POSITIVE EXOSOMES" in the name of Antonio Chiesi et al., which claims priority to European Patent Application No. 17177190.0 filed on Jun. 21, 2017, both of which are hereby incorporated by reference herein in their entirety.

FIELD OF THE INVENTION

The present invention relates to methods for the isolation of tumour-derived exosomes by immunocapture with an anti CA-IX antibody, to methods for quantifying tumour-related nucleic acid sequences from such isolated exosomes and to methods for determining in vitro the presence of a tumour in a subject. The invention also relates to kits for use in these methods.

BACKGROUND TO THE INVENTION

Exosomes are 30-100 nm diameter membraneous vesicles of endocytic origin. They are natural lipidic extra cellular nanovescicles produced and released by virtually all cell types in a finely regulated and functionally relevant manner so that the protein and nucleic acid sequences composition reflects the type and condition of a parent cell. These vesicles have intrinsic stability and ability to cross biological barriers, so that exosomes originated from different tissues can be found in easily accessible biological fluids such as blood. Given their biological roles and features, exosomes are considered early sentinels of alterations in cell and tissue homeostasis and metabolism and are an appealing source for identification of novel disease-relevant biomarkers as well as display of known tissue markers in a liquid biopsy paradigm. This is a major premise and promise of using exosome targeted assays in diagnostics of complex diseases such as cancer. The major challenge lies in association of exosome associated markers to a particular tissue, in a particular condition and optimization of reliable, affordable, noninvasive exosome targeted solutions and assays that can be realistically implemented in clinical research and practice.

There is a need to develop methods and relative kits that are able to isolate tumour-derived exosomes from biological samples, and to detect and quantify in a meaningful way tumor-related nucleic acid sequences such as BRAF gene point mutations BRAFV600E, BRAFV600K, BRAFV600R, BRAFV600M and BRAFV600D, Wild Type (WT) BRAF gene amplification (4,5), KRAS gene point mutations such as KRAS G12C, KRAS G12S, KRAS G12V, KRAS G12A, KRAS G12D, KRAS G13D and KRAS WT gene amplification (6), NRAS gene point mutations such as NRAS G12C and NRAS G12D, NRAS Q61K, NRAS Q61R (7,8), epidermal growth factor receptor (EGFR) gene point mutations such as EGFRT790M, EGFR L858R, EGFR EXON 19 deletion, EGFR EXON 20 deletion (9,10), c-Myc gene amplification and overexpression (11,12), retrotrasposon RNA transcripts such as short and long interspersed nuclear element (SINE, LINE) and human endogenous retroviral repeats (HERV) (12), androgen receptor (AR) gene point mutations such as AR L702H, AR W742C, AR H875Y, AR F877L, AR T878A, splicing variant AR-V7 and AR WT gene amplification (13-15).

PRIOR ART

Carbonic anhydrase IX (CA-IX) is known tumor biomarker with diagnostic and prognostic value and a potential target for the development of anti-cancer drugs (1-2). A soluble form of CA-IX can be detected in the serum of cancer patients (3). W02012115885 cites CA-IX as a biomarker that can be measured from exosomes. Dorai (16), describes how Renal Carcinoma cells, when forced to over-express CA-IX, increase the shedding of exosomes.

Anti CA-IX antibodies, whether monoconal or polyclonal, and directed to various species such as human, rat, or mice and are commercialy available from, for example, ThermoFisher Scientific Inc.

DETAILED DESCRIPTION OF THE INVENTION

Figure 1:
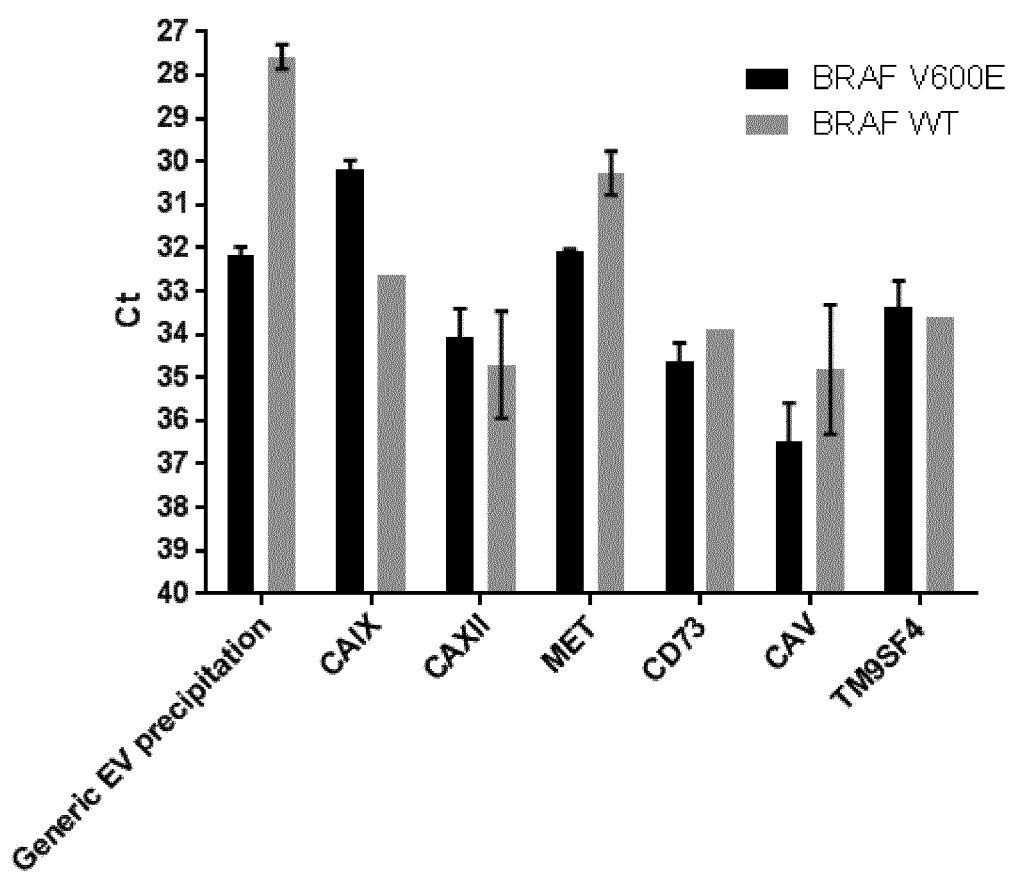
FIG. 1 depicts the BRAF and BRAFV600E levels measured from exosomes isolated from a V600E positive patient plasma by either generic precipitation of by immunocapture with various antibodies, including CA-IX.

We have surprisingly found that when an anti CA-IX antibody is used to capture exosomes from a biological fluid, it allows for the isolation of tumour-derived exosomes.

Accordingly, in a first aspect of this invention, there is provided a method for the in vitro isolation of tumour-derived exosomes from a biological fluid, such method comprising capturing exosomes from a sample of that biological fluid with an anti CA-IX antibody.

We have also surprisingly found that when an anti CA-IX antibody is used to capture exosomes from a biological fluid, it allows for the meaningful detection and quantification of tumour-related nucleic acid sequences, and to discriminate between patients that are affected by a tumour and those that are not.

Accordingly, in a second aspect of this invention, there is provided a method for the in vitro quantification of a tumour-related nucleic acid sequence from a biological fluid, such method comprising
   a) capturing exosomes from a sample of such biological fluid with an anti CA-IX antibody, and
   b) detecting the level of tumour-related nucleic acid sequence present in the exosomes captured in step a).

In a third aspect of this invention, there is provided a method to determine in vitro the presence of a tumour in a subject comprising
 a) capturing exosomes from a biological fluid sample from that subject with an anti-CA-IX antibody
 b) determing the level of a tumour-related nucleic acid sequence present in the exosomes isolated in step a), and
 c) comparing the level of tumour-related nucleic acid sequence determined in step b) with one or more reference values.

In a fourth aspect of this invention, there is provided a kit for use in the isolation of tumour-derived exosomes from a biological fluid, such kit comprising an anti CA-IX antibody.

In a fifth aspect of this invention, there is provided a kit for use in the quantification of a tumour-related nucleic acid sequence in exosomes from a biological fluid, such kit comprising an anti CA-IX antibody.

In a sixth aspect of this invention, there is provided a kit for use in determining in vitro the presence of a tumour in a subject from exosomes isolated from a biological fluid, such kit comprising an anti CA-IX antibody.

In a specific embodiment under the fifth and sixth aspect of this invention, the kit further comprises a set of primers directed to the tumour-related nucleic acid sequence.

In one embodiment under any aspect the tumour is selected form the list of lung cancer, breast cancer, bladder cancer, renal cancer, prostate cancer, colorectal cancer, gastric cancer, ovarian cancer and melanoma.

In one embodiment under any aspect of this invention, the biological fluid is selected from the list of blood, plasma, serum, urine and saliva.

In one embodiment under any aspect of this invention, the tumour-related nucleic acid sequence is selected from the list of a double stranded DNA sequence, a single strand DNA sequence and an RNA sequence.

In one embodiment, the double stranded DNA tumour-related nucleic acid sequence is a wild-type sequence from a target gene selected from the group consisting of the BRAF gene, the KRAS gene, the NRAS gene, the EGFR gene, the AR gene.

In another embodiment, the the double stranded DNA tumour-related nucleic acid sequence is mutated sequence from a target gene selected from the group consisting of the BRAF gene, the KRAS gene, the NRAS gene, the EGFR gene, the AR gene. In a specific embodiment, the mutated sequence is selected from the list of an amplification, a point mutation, a deletion and an insertion.

In one embodiment, the double stranded DNA tumour-related nucleic acid sequence is selected form the list of a WT BRAF gene amplification, a BRAF gene point mutation, a WT KRAS gene amplification, a KRAS gene point mutation, an WT NRAS gene amplification, an NRAS gene point mutation, a WT cMyc gene amplification, a WT EGFR gene amplification, an EGFR gene point mutation, an EGFR gene deletion, an EGFR gene insertion, the WT AR gene, an AR gene point mutation.

In one embodiment, the single stranded DNA tumour-related nucleic acid sequence is selected from the list of a WT cMyc gene amplification, a long interspersed nuclear element (LINE) retrotransposon, a short interspersed nuclear element (SINE) retrotransposon and a human endogenous retrovirus (HERV) retrotransposon.

In one embodiment, the HERV retrotransposon is selected from the list of HERV-H, HERV-K, HERV-C and HERV-W.

In one embodiment, the RNA sequence is selected from the list of WT cMyc mRNA, LINE mRNA, SINE mRNA, HERV mRNA, WT androgen receptor (AR) mRNA, and AR gene splicing variant mRNA.

In one embodiment, the HERV mRNA sequence is selected from the list of HERV-H mRNA, HERV-K mRNA, HERV-C mRNA and HERV-W mRNA.

In one embodiment, the BRAF gene point mutation is a BRAF V600 mutation.

In a specific embodiment, the BRAFV600 mutation is selected from the list of BRAFV600E, BRAFV600K, BRAFV600R, BRAFV600M and BRAFV600D.

In one embodiment, the KRAS gene point mutation is a KRAS G12 mutation.

In a specific embodiment, the KRAS G12 mutation is selected from the list of KRAS G12C, KRAS G12S, KRAS G12V, KRAS G12A and KRAS G12D.

In one embodiment, the KRAS gene point mutation is a KRAS G13 mutation.

In a specific embodiment, the KRAS G13 mutation is KRAS G13D.

In one embodiment the NRAS gene point mutation is an NRAS G12 mutation.

In a specific embodiment, the NRAS G12 mutation is selected from the list of NRAS G12C and NRAS G12D.

In one embodiment the NRAS gene point mutation is an NRAS Q61 mutation.

In a specific embodiment, the NRAS Q61 mutation is selected from the list of NRAS Q61K and NRAS Q61R.

In one embodiment EGFR gene point mutation is an EGFR T790 mutation.

In a specific embodiment, the EGFR T790 mutation is EGFRT790M.

In one embodiment EGFR gene point mutation is an EGFR L858 mutation.

In a specific embodiment, the EGFR L858 mutation is EGFR L858R.

In one embodiment EGFR gene deletion is an EGFR EXON 19 deletion.

In one embodiment EGFR gene insertion is EGFR EXON 20 insertion.

In one embodiment, the AR gene point mutation is selected from the list of an AR L702 mutation, an AR W742 mutation, and AR H875 mutation, an AR F877 mutation, and an AR T878 mutation.

In a specific embodiment, the AR L702 mutation is AR L702H.

In a specific embodiment, the AR W742 mutation is AR W742C.

In a specific embodiment, the AR H875 mutation is AR H875Y.

In a specific embodiment, the AR F877 mutation is AR F877L.

In a specific embodiment, the AR T878 mutation is AR T878A.

In one embodiment, the AR gene splice variant is AR-V7.
All embodiments may be combined.

EXAMPLES

The invention is now described by means of non-limiting examples. Some of the nucleotide sequences cited in the examples contain one or more LNA nucleosides, which are identified by the symbol "+" followed by the relevant letter (A, C, G or T/U). The structural formulas of the LNA-modified nucleosides are illustrated herein below:

| LNA-unit | Formula |
|---|---|
| LNA-Adenosine | (structure of LNA-Adenosine) |
| LNA-Thymdine | (structure of LNA-Thymidine) |
| LNA 5-Methylcytidine | (structure of LNA 5-Methylcytidine) |
| LNA Guanosine | (structure of LNA Guanosine) |

Materials & Methods

A) Blood collection and Fractionation

All patients had been fasting since midnight before blood collection in the morning. The blood was collected in K2-EDTA tubes for plasma (VACUTAINER® Becton Dickinson, purple cap, REF 367864, 6.0 ml) or regular tubes for serum (VACUTAINER® Becton Dickinson, red cap, REF 366881, 5.0 ml). Tubes were subsequently inverted 5 or 6 times, kept in a vertical position and stored at room temperature (20-25° C.). Further processing was performed within an hour from collection by centrifugation at 1500 g for 15 minutes at 20-25° C. The plasma was collected using a disposable Pasteur pipette (Steroglass, REF: LPMW032653; 5 ml), avoiding to resuspend it by stopping 3-4mm above the buffy coat. Samples were visually checked for traces of lipids, bile (Itterum) or hemolysis. Plasma was collected in 15ml Falcon tubes, gently inverted, and aliquoted in labeled cryotubes (REF: n° BSM 535, Biosigma) and stored at −80° C.

B) Plasma and Reagent's Preparations

Plasma samples were centrifuged at 1200 g for 20 minutes at room temperature (RT) to eliminate red blood cells and cellular debris. The supernatant was then collected and centrifuged once again 10000 g for 30 minutes at RT to eliminate larger vesicles and debris. The resulting supernatant was collected and diluted in a volume ratio 1:1 of phosphate buffer (PBS). One microliter of protease inhibitor cocktail (1000×; Sigma Cat. num. P-834) was added to each sample to preserve protein biomarkers. Reagents for DNA purification, including washing buffers, were prepared according to the manufacturer's instructions (HansaBioMed OU, Estonia). Primers and probes were reconstituted in Milli-Q water or TE-buffer, aliquoted, and stored at −20° C. until use.

C) Isolation of Exosomes from Plasma

Anti-CAIX- and anti-CAXII antibodies used for capturing tumor-derived exosomes were kindly provided by Dr Reinhard Zeidler (Helmoltz Zentrum Munchen, Germany). Anti-cMET (Cat. Num. PAS-27235; Thermo Fisher), anti-CD73 (Cat. Num. ab91086; Abcam), anti-CAV (Cat. Num. 611338; BD Biosciences), anti-TM9SF4 (Cat Num.: LS-A9852; Lifespan Biosciences, Inc) and anti- Anti-EP-CAM (Cat. Num. PAS-29634; Thermo Fisher) antibodies were purchased from commercial providers. Latex beads were purchased from a commercial provider (HansaBioMed OU, Estonia) and coated using 1ug of antibody per sample. To isolate a generic exosome population, the Vn96 peptide was used according to the manufacturer's instructions (ME-kit, New England Peptide, US).

Ten microliters of antibody-coated beads or 50 μs of Vn96 peptide were added to the pre-cleared diluted plasma sample to isolate exosomes. Samples were mixed by pipetting up and down and incubated for two hours at RT under rotation. Following incubation, samples were centrifuged at 5000 g for 10 minutes at RT. The obtained supernatant was then carefully discarded without disturbing the bead pellet. The pellet was washed with PBS and spun down by centrifugation at 5000 g for 10 minutes. The wash step was then repeated one more time and the final pellet was resuspended in 200 μl of PBS 1×.

D) Isolation of Exosomes from Urine

Prior to isolation, urine was concentrated 10× using EMD Millipore Amicon Ultra-15 filter units with a cutoff of 100kDa (cat.num. UFC910024, Millipore).

Ten microliters of anti-CAIX coated beads were then spiked into 1 mL of concentrated urine. After 2-hour isolation, beads were pelleted and washed as previously described before RNA extraction.

E) DNA Purification and Concentration

Exosome-associated DNA (EV-DNA) was extracted and concentrated using a commercially available kit for circulating DNA extraction (EXO-DNAc-PS; HansaBioMed OU, Estonia). Briefly, bead-bound exosomes were lysed with a proprietary lysis buffer and digested with proteinase K to release the DNA from protein complexes. The sample was then supplemented with ethanol, loaded onto a silica membrane spin column and centrifuged at 10000 g for 1 minute. Following centrifugation, the flow-through was discarded. Two washing steps were performed according to the manufacturer's instructions to get rid of contaminating solvents and plasma-derived inhibitors before elution. The eluted DNA was supplemented with binding buffer and ethanol and loaded onto a new silica membrane spin column one more time for further purification and concentration. Two more washing steps were applied before eluting the purified EV-DNA in a final volume of 15 µl of elution buffer provided by the kit.

F) RNA Purification

RNA was extracted directly from the bead pellet using using a commercially available kit for exosomal RNA extraction (sortEV™; Exosomics Siena Spa). Briefly, bead-bound exosomes were lysed with a phenol-based buffer and vortexed for 30 seconds. The sample was then supplemented with chlorophorm and spun down at 12000 g for 10 minutes in order to separate the acqueous from the organic phase. Following centrifugation, the acqueous phase was collected, supplemented with ethanol and loaded onto a silica membrane spin column. The loaded column was centrifuged at 14000 g for 30 seconds and the flow-through was discarded. Two washing steps were performed according to the manufacturer's instructions to get rid of contaminating solvents and plasma-derived inhibitors before elution. The purified EV-RNA was eluted in a final volume of 15 µl of elution buffer provided by the kit.

G) PCR Amplification of BRAF, KRAS, EGFR, cMyc Genes from EV-DNA

PCR amplification of EV-DNA is challenging due to low abundance and high fragmentation of the template. Therefore, a pre-amplification step was included in the protocol upstream of the quantitative real-time PCR (qPCR) to improve detection of the target genes BRAF and KRAS.

Primers and Probes

```
BRAF preamp primers:
a) WT FW:
                                    (SEQ ID NO: 1)
5'-TAGGTGATTTTGGTCTAGCTACAG + T-3';

b) WT RW:
                                    (SEQ ID NO: 2)
5'-TTAATCAGTGGAAAAATAGCCTCA-3';

c) V600E FW:
                                    (SEQ ID NO: 3)
5'-TAGGTGATTTTGGTCTAGCTACAG + A-3';

d) V600E RW:
                                    (SEQ ID NO: 4)
5'-TTAATCAGTGGAAAAATAGCCTCA-3';

KRAS preamp primers:
a) WT FW:
                                    (SEQ ID NO: 5)
5'-GGTAGTTGGAGCTGGTGGC-3';

b) RW:
                                    (SEQ ID NO: 6)
5'-TGATTCTGAATTAGCTGTATCGTCAA-3';

BRAF qPCR primers and probe:
a) WT: FW:
                                    (SEQ ID NO: 7)
5'-TAGGTGATTTTGGTCTAGCTACAG + T-3';

b) WT RW:
                                    (SEQ ID NO: 8)
5'-TTAATCAGTGGAAAAATAGCCTCA-3';

c) V600E FW:
                                    (SEQ ID NO: 9)
5'-TAGGTGATTTTGGTCTAGCTACAG + A-3';

d) V600E RW:
                                    (SEQ ID NO: 10)
5'-TTAATCAGTGGAAAAATAGCCTCA-3';

e) Probe:
                                    (SEQ ID NO: 11)
5'-FAM-CCGAAGGGGATC + CAGACAA +
CTGTTCAAACTGCCTTCGG-3BHQ1-3';

KRAS qPCR primers and probes:
a) WT FW:
                                    (SEQ ID NO: 12)
5'-GGTAGTTGGAGCTGGTGGC-3';

b) RW:
                                    (SEQ ID NO: 13)
5'-TGATTCTGAATTAGCTGTATCGTCAA-3';

c) Probe:
                                    (SEQ ID NO: 14)
5'-FAM-CACTCTTGCCTACGC-MGB-3';

EGFR qPCR primers and probes
a) FW:
                                    (SEQ ID NO: 15)
5'-GCAGCATGTCAAGATCACAGATT-3';

b) RW:
                                    (SEQ ID NO: 16)
5'-CCTCCTTCTGCATGGTATTCTTTCT-3';

c) probe WT (VIC):
                                    (SEQ ID NO: 17)
5'-AGTTTGGCCAGCCCAA-3';

cMyc qPCR primers and probes
a) FW:
                                    (SEQ ID NO: 18)
5'-CCCTCCACTCGGAAGGACTATC-3';

b) RW:
                                    (SEQ ID NO: 19)
5'-AGGACTCTGACACTGTCCAACT-3';

c) probe WT (VIC):
                                    (SEQ ID NO: 20)
5'-TGACCCTCTTGGCAGCAG-3';
```

Pre-Amplification of Target Genes from EV-DNA

All the reagents were thawed at RT for at least one hour and briefly mixed without vortexing to avoid inactivation of the enzyme. Each pre-amplification reaction included 7 µl of eluted DNA, 1× Bioron High Fidelity Buffer, 3 mM $MgCl_2$; 200 µM dNTPs, 1,25 Units of SNPase polymerase (Bioron GmbH, Germany) and 0,4 µl of primers (10 µM) in a total volume of 20 µl. Each reaction was performed in a PCR-compatible microvial loaded onto a thermal PCR cycler running the following PCR program: 98° C. for 30", 98° C. for 10" and 72° C. for 5', 4° C. on hold. The pre-amplified DNA was diluted in 80 µl of sterile water and immediately used for qPCR analysis or stored at −20° C. for up to three months.

Amplification of Target Genes by qPCR

For amplification of target genes from EV-DNA, each qPCR reaction included 7 µl of pre-amplified DNA, 1× SsoAdvanced Universal Probes Mastermix (Biorad; US), 0.625 µl of primers (10 µM) and 0.3125 µl of fluorescent probe (10 µM) in a total volume of 25 µl. After careful mixing, each reaction was loaded in duplicate on a 96-well PCR plate and the following qPCR program was launched: 95° C. for 3', 40 cycles at 95° C. for 5" and 60° C. for 30", followed by a final hold step at 4° C. For amplification of target genes from EV-RNA, one microliter of EV-RNA was directly loaded into a 20-μl One-step RT-qPCR reaction and amplified according to the manufacturer's instructions (iTaq Universal OneStep qPCR; Biorad).

Amplification of Retrotransposon Elements by qPCR

One microliter of EV-DNA or EV-RNA were directly loaded in the qPCR mix and amplified as previously described. The following primers and probes were used:

```
LINE qPCR primers and probes
a) FW:
                                        (SEQ ID NO: 21)
5'-TCAACAAGAAGAGCTAACTATCC-3';

b) RW:
                                        (SEQ ID NO: 22)
5'-TTGTAGGTCACTCAGGACTTGC-3';

c) probe
                                        (SEQ ID NO: 23)
(5,6-TAMRA)-TGCACCCAATACAGGAGCACCCAGATTCA-BHQ2;

HERV-W qPCR primers and probes
a) FW:
                                        (SEQ ID NO: 24)
5'-CTTCCAGAATTGAAGCTGTAAAGC-3';

b) RW:
                                        (SEQ ID NO: 25)
5'-GGGTTGTGCAGTTGAGATTTCC-3';

c) Probe
                                        (SEQ ID NO: 26)
FAM-5'-TTCTTCAAATGGAGCCCCAGATGCAG-3'-TAMRA;
```

Q-PCR data analysis and interpretation of results

Quantification of the target genes BRAF and KRAS WT was expressed as threshold cycle (Ct) values and plotted on an inverted Y axis. Alternatively, a Zscore value was used to define a threshold to distinguish healthy from disease samples as previosly published (15).

Briefly, samples with positive Zscore value were considered disease-negative while samples with negative Zscore were classified as cancer-positive. In some isolated cases the opposite pattern was also observed as a result of the downreguation of levels of retrotransposon elements.

Amplification of Target Genes by Digital PCR

A chip-based digital PCR (dPCR) platform (QuantStudio 3D Digital PCR System Platform, Thermo Fisher Scientific, Carlsbad, CA, USA) was used for mutation detection. The dPCR mutation detection was based on a TaqMan-MGB probe conjugated with FAM targeting the AR T878A mutation TaqMan-MGB probe conjugated with VIC targeting the corresponding wild-type gene (SNP Genotyping Assay C 175239649 10; Fisher Scientific). AR-WT and AR-V7 splicing variant assays were custom-made with the following primers and probes:

```
                                        (SEQ ID NO: 27)
a) AR-WT FW:    5'-CAGCCTATTGCGAGAGAGCTG-3';

(SEQ ID NO: 28)
b) AR-WT RW:    5'-GAAAGGATCTTGGGCACTTGC-3';

(SEQ ID NO: 29)
c) Probe AR-WT: MGB 5'-AGTTCACTTTTGACCTGC-3';

(SEQ ID NO: 30)
d) AR-V7 FW:    5'-CCATCTTGTCGTCTTCGGAAATGTTA-3';

(SEQ ID NO: 31)
e) AR-V7 RW:    5'-TTTGAATGAGGCAAGTCAGCCTTTCT-3';

(SEQ ID NO: 32)
f) Probe AR-V7: MGB 5'-AAGCAGGGATGACTCTG-3'.
```

Sixteen microliters of reaction mix containing 80 of 2× QuantStudio 3D Digital PCR Master Mix (Life Technologies), 0.40 μl of 40× TaqMan-MGB-FAM-probe assay, 1.10 of diluted DNA (50 ng/μl) and 6.50 of nuclease-free water (Qiagen) were prepared in the reaction mix. The negative controls reaction mix contained 80 of 2× QuantStudio 3D Digital PCR Master Mix, 0.4 μl of 40× TaqMan-MGB-FAM-probe assay and 7.60 of nuclease-free water.

To quantify AR T878A, AR-V7 and wt gene copies, 150 of reaction mix were loaded onto a QuantStudio 3D Digital PCR 20K Chip using the automatic chip loader according to the manufacturer's instructions (Life Technologies). The loading splits the reaction into 20.000 micro-reactions of final volume of 865pL, corresponding to the 20.000 microwells onto the surface of the chip. Each loaded chips underwent the following cycling conditions using the Pro-Flex PCR System: 95° C. for 8', 40 cycles at 95° C. for 15" and 60° C. for 1', followed by a final extension step at 60° C. for 2'. After thermocycling, the chips were imaged on the QuantStudio 3D Instrument which calculates the estimated concentration of the nucleic acid sequence targeted by the probe. Data analysis was performed using the QuantStudio 3D Analysis Suite Cloud Software after manually setting up the analytical threshold and excluding aberrant emissions. All negative controls signal resulted under the value of 5000 RFU in FAM, so this threshold was fixed for the discrimination of positive and negative emission for AR T878A, while 2100 RFU in VIC resulted as threshold of emission of AR wt. We also considered negative those samples with equal or less than 2 copies of mutant per ml.

Example 1

Capturing Exosomes with Anti CA-IX Antibody Allows for an Enrichment in Tumour-Derived Exosomes FIG. 1 shows the results of a quantitative analysis of the BRAF wild type (WT) and V600E mutated gene by real time quantitative PCR (qPCR) on DNA extracted from BRAF V600E-positive melanoma patient's plasma following exosome immunoisolation with anti-carbonic anhydrase IX (CAIX)-, anti-carbonic anhydrase XII (CAXII)-, anti-cMET-, anti-CD73-, anti-caveolin (CAV)- and anti-TM9SF4-antibody-coated beads or generic extracellular vesicle (EV) precipitation. The antibodies were selected based on their ability to target known tumor biomarkers. Immunoisolation with anti-CAIX-antibodies enriched for more tumor-derived exosomes than all other immunocapture approaches and the generic EV precipitation as suggested by the higher levels of BRAF V600E gene compared to the BRAF WT gene. Data are expressed as threshold cycle (Ct) values and plotted on an inverted Y scale.

Example 2

Figure 2:
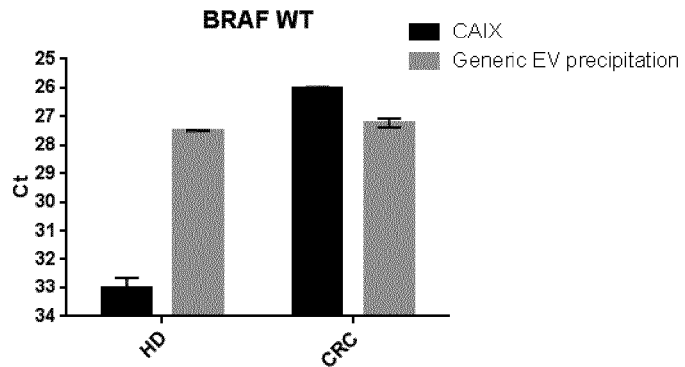
FIG. 2A and B depict the BRAF gene levels measured in exosomes isolated from the plasma of healthy, colorectal cancer or melanoma patients either by immunocapture an anti CA-IX antibody or by generic precipitation.
FIG. 2C depicts the allelic frequency of the AR T878 as measured from exosomes isolated from plasma of prostate cancer patients by immunocapture with an anti CA-IX antibody or by generic EV precipitation.
Figure 2:
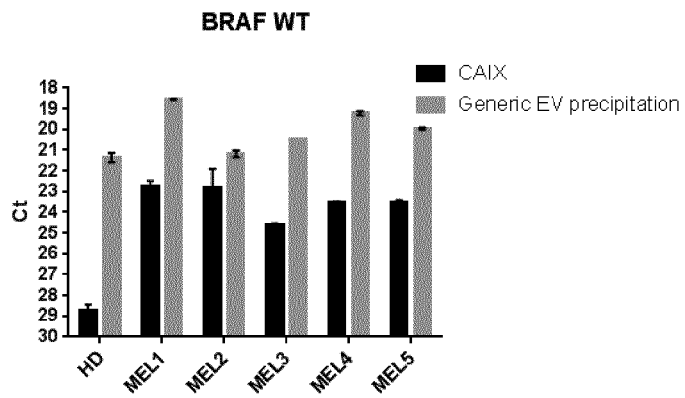
Figure 2:
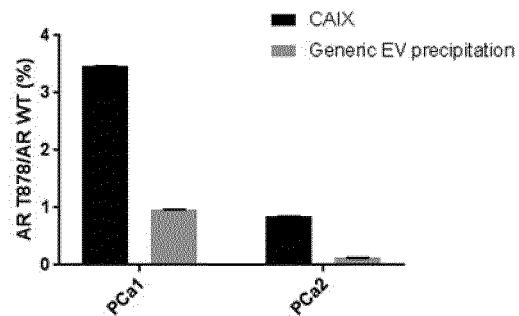

Compared to Generic Isolation of Exosomes by Ultracentrifugation, Immunocapture with a Anti CA-IX Antibody Allows to Discriminate Between Healty and Cancer Patients FIGS. 2 and B shows the results of a quantitative analysis of the BRAF WT gene by qPCR on DNA extracted from healthy donors (HD) and A) colorectal cancer (CRC) or B) metastatic melanoma (MEL) patient plasma following exosome immunoisolation with anti-CAIX-antibody-coated beads or generic extracellular vesicle (EV) precipitation. Tumor exosome-derived BRAF WT gene levels were found to be significantly higher in both CRC and MEL patient's plasma compared to healthy donor plasma samples following anti-CAIX-immunocapture suggesting the isolation of CAIX-positive tumor-derived exosomes. Conversely, no difference was observed between cohorts after generic EV precipitation due to the co-isolation of non tumor-derived exosomes bearing copies of the BRAF WT gene. Data are expressed as threshold cycle (Ct) values and plotted on an inverted Y scale. In a similar way, FIG. 2C shows the result of a quantitative analysis of the AR T878 vs AR WT allelic frequency in two prostate cancer (PCa) patients.

Example 3

Figure 3:
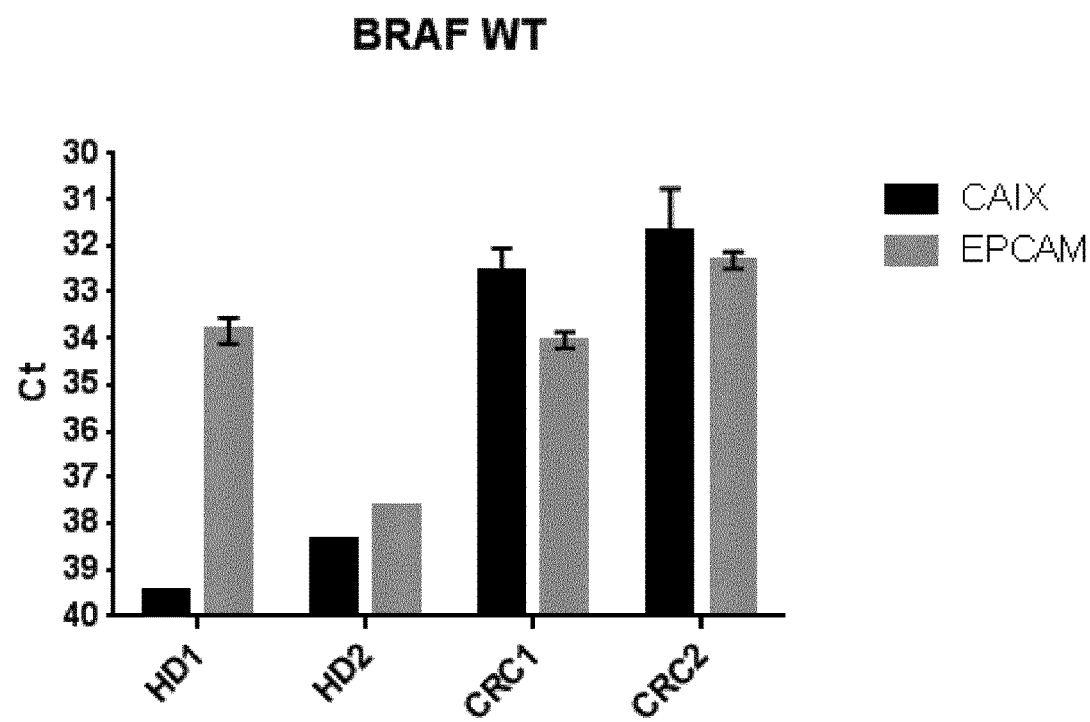
FIG. 3 depicts the BRAF gene levels measured in exosomes isolated from the plasma of healthy or colorectal cancer patients either by immunocapture with an anti CA-IX antibody or immunocapture an with anti EPCAM antibody.

Compared to Isolation of Exosomes by Immunocapture with an Anti-EPCAM Antibody, Immunocapture with a Anti CA-IX Antibody Allows to Discriminate Between Healty and Cancer Patients FIG. 3 shows the results of a quantitative analysis of the BRAF WT gene by qPCR on DNA extracted from HD patients and CRC patients plasma following exosome immunoisolation with anti-CAIX-antibody-coated beads or anti-epithelial cell adhesion molecule (EPCAM)-antibody-coated beads. EPCAM was chosen as reference tumor-exosome marker. Exosomes isolated using anti-CAIX-antibody-coated beads had low levels of BRAF WT gene in both HD plasma samples and high levels in both CRC samples. Conversely, exosomes isolated with anti-EPCAM-antibody-coated beads had high levels of BRAF WT gene levels in one HD sample and in both CRC samples likely due to the lower ability of anti-EPCAM antibodies to efficiently isolate CRC-derived-exosomes as compared to anti-CAIX-antibodies. Data are expressed as threshold cycle (Ct) values and plotted on an inverted Y scale.

Example 4

Diagnosis of Colorectal Cancer with BRAF

Figure 4:
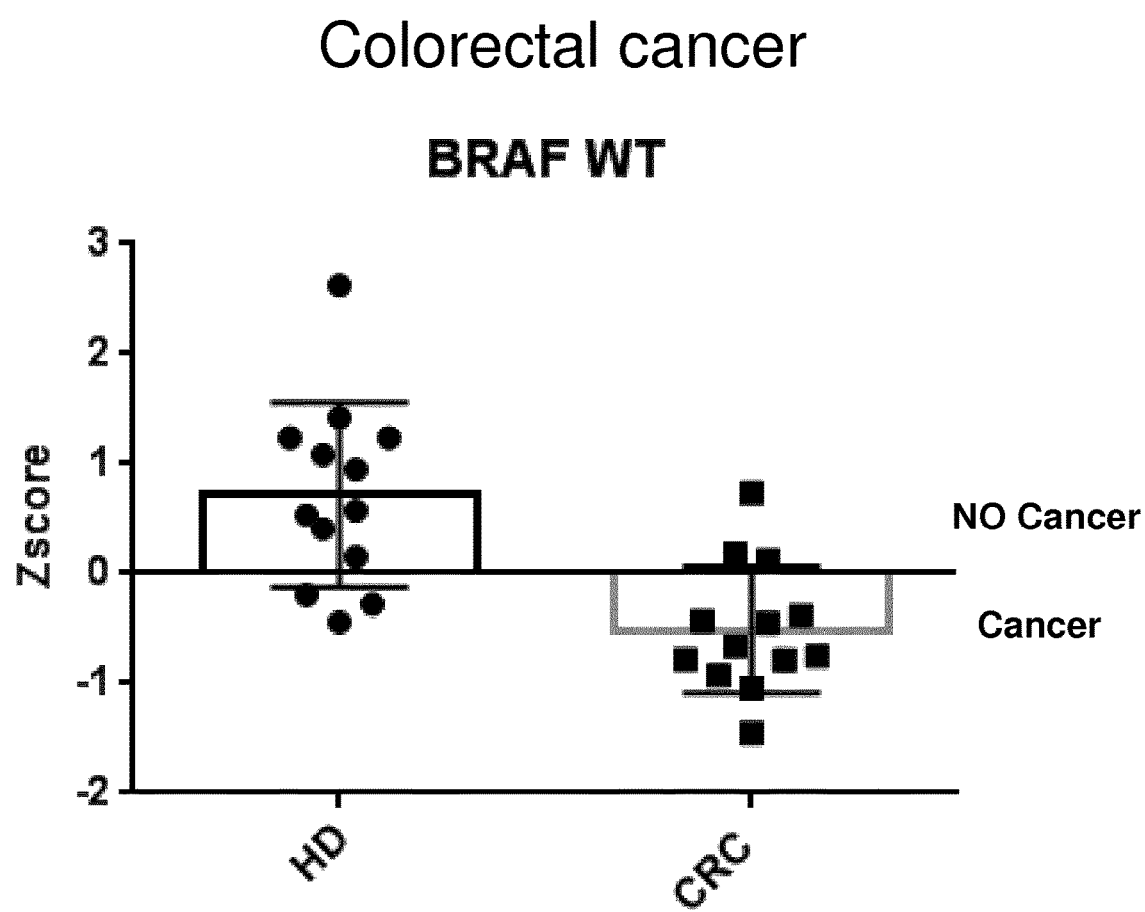
FIG. 4 depicts the Z score of BRAF levels as measured from exosomes isolated from the plasma of healthy or colorectal cancer patients by immunocapture with an anti CA-IX antibody.

FIG. 4 shows the results of a quantitative analysis of the BRAF WT gene by qPCR on DNA extracted from HD patients (n=13) and CRC patients (n=13) plasma following exosome immunoisolation with anti-CAIX-antibody-coated beads. Zscore value of 0 was used as diagnostic threshold. Samples with positive Zscore were considered cancer negative while those with negative Zscore as cancer positive. In this experiment, 10 out of 13 (80%) HD samples had positive Zscore and were considered as cancer negative. Conversely, 10 out of 13 (80%) CRC samples had negative Zscore and were considered as cancer positive. These data define a diagnostic threshold for distinguishing healthy individuals from CRC patients with the described test.

Example 5

Diagnosis of Prostate Cancer with BRAF

Figure 5:
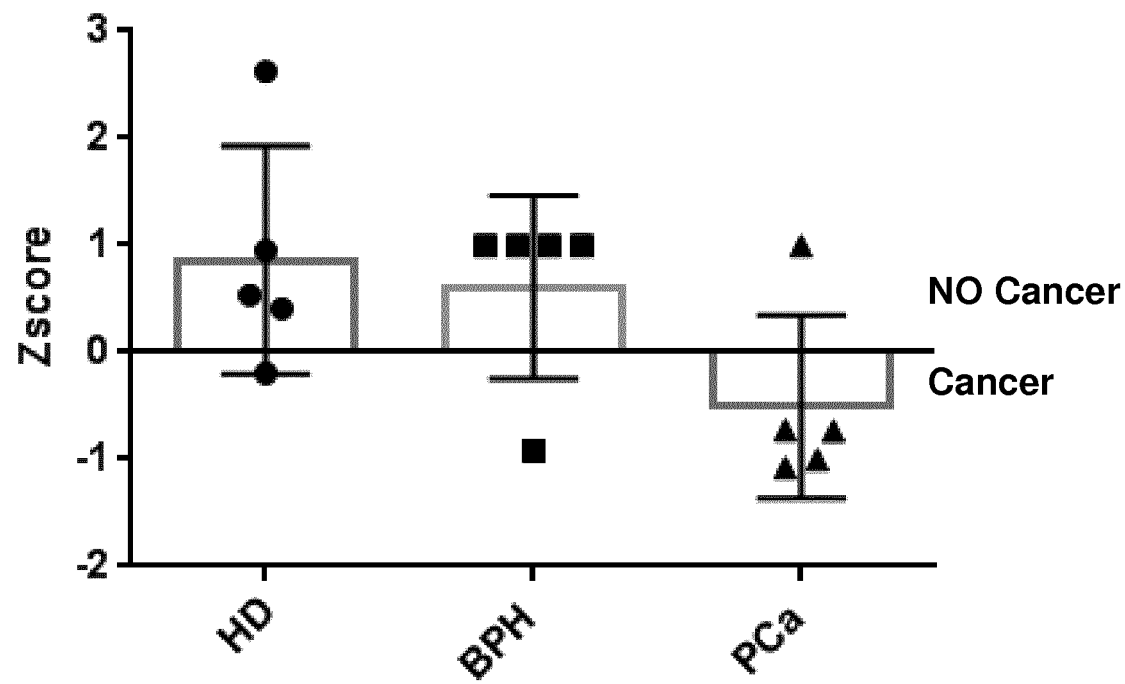
FIG. 5 depicts the Z score of BRAF levels as measured from exosomes isolated from the plasma of healthy or prostate cancer patients by immunocapture with an anti CA-IX antibody.

FIG. 5 shows the results of a quantitative analysis of the BRAF WT gene by qPCR on DNA extracted from HD patients (n=5), benign prostatic hyperplasia (BPH; n=5) and prostate cancer (Pca; n=5) patients following exosome immunoisolation with anti-CAIX-antibody-coated beads. Zscore value of 0 was used as diagnostic threshold as previously described. In this experiment, 4 out of 5 (80%) HD or BPH plasma samples had positive Zscore and were considered as cancer negative. 4 out of 5 (80%) of PCa samples had negative Zscore and were considered as cancer positive. These data define a diagnostic threshold for distinguishing healthy individuals or BPH patients from PCa patients with the described test.

Example 6

Diagnosis of Gastric Cancer with BRAF

Figure 6:
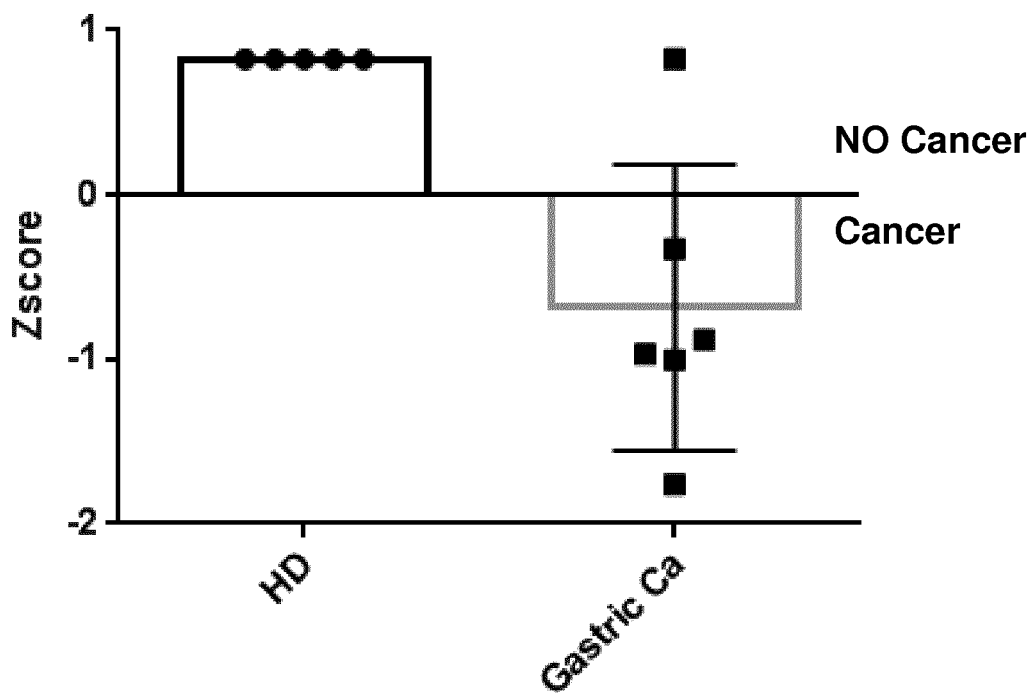
FIG. 6 depicts the Z score of BRAF levels as measured from exosomes isolated from the plasma of healthy or gastric cancer patients by immunocapture with an anti CA-IX antibody.

FIG. 6 shows the results of a quantitative analysis of the BRAF WT gene by qPCR on DNA extracted from HD patients (n=5), and gastric cancer (Gastric Ca; n=6) patients following exosome immunoisolation with anti-CAIX-antibody-coated beads. Zscore value of 0 was used as diagnostic threshold as previously described. In this experiment, 5 out of 5 (100%) HD plasma samples had positive Zscore and were considered as cancer negative. 5 out of 6 (83%) PCa samples had negative Zscore and were considered as cancer positive. These data define a diagnostic threshold for distinguishing healthy individuals from gastric cancer patients with the described test.

Example 7

Diagnosis of Ovarian Cancer with BRAF

Figure 7:
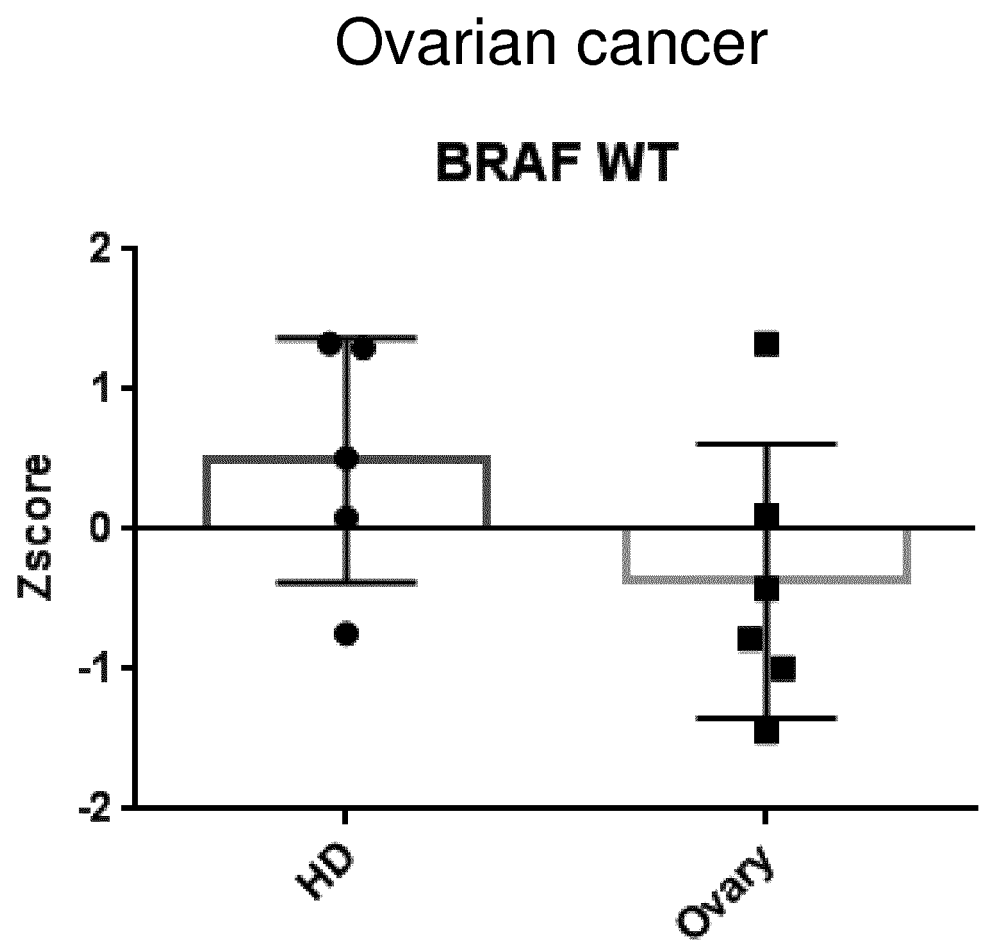
FIG. 7 depicts the Z score of BRAF levels as measured from exosomes isolated from the plasma of healthy or ovarian cancer patients by immunocapture with an anti CA-IX antibody.

FIG. 7 shows the results of a quantitative analysis of the BRAF wild type (WT) gene by real time PCR on DNA extracted from HD patients (n=5), and ovarian cancer (Ovary; n=6) patients following exosome immunoisolation with anti-CAIX-antibody-coated beads. Zscore value of 0 was used as diagnostic threshold as previously described. In this experiment, 4 out of 5 (80%) HD plasma samples had positive Zscore and were considered as cancer negative. 4 out of 6 (66%) PCa samples had negative Zscore and were considered as cancer positive. These data define a diagnostic threshold for distinguishing healthy individuals from ovarian cancer patients with the described test.

Example 8

Diagnosis of Colorectal or Prostate Cancer with KRAS

Figure 8:
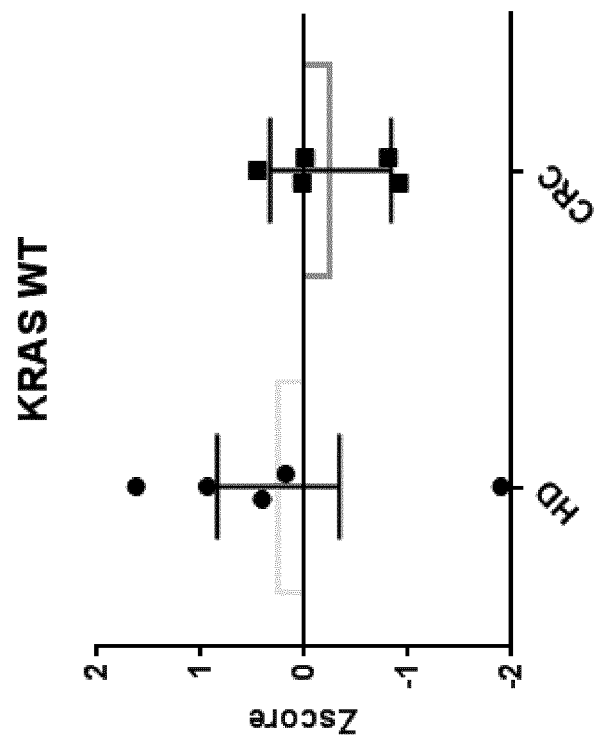
FIG. 8 depicts the Z score of KRAS levels as measured from exosomes isolated from the plasma of healthy, colorectal cancer, benign prostate hyperplasia or prostate cancer patients by immunocapture with an anti CA-IX antibody.
Figure 8:
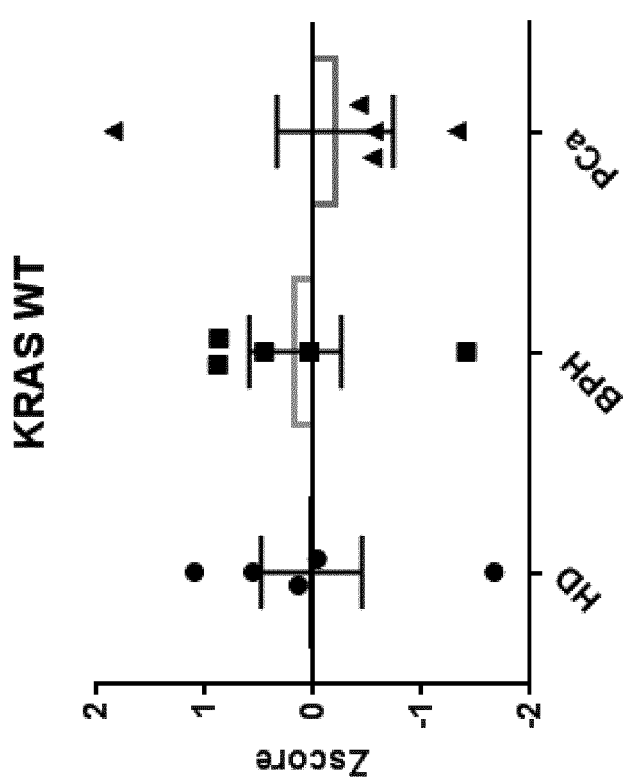

FIG. 8 shows the results of a quantitative analysis of the KRAS wild type (WT) gene by real time PCR on DNA extracted from HD, BPH and cancer patients samples following exosome immunoisolation with anti-CAIX-antibody-coated beads. Zscore value of 0 was used as diagnostic threshold as previously described. A) 4 out of 5 (80%) HD plasma samples had positive Zscore and were considered as cancer negative while 4 out of 5 (80%) CRC plasma samples had negative Zscore and were considered as cancer positive. B) 4 out of 5 (80%) HD and BPH plasma samples had positive Zscore and were considered as cancer negative while 4 out of 5 (80%) PCa plasma samples had negative Zscore and were considered as cancer positive. Overall, these data indicate that a diagnostic threshold for distinguishing healthy individuals or benign disease patients from cancer patients can be generated using KRAS WT gene instead of BRAF WT gene as PCR readout.

Example 9

Diagnosis of Lung Cancer with EGFR

Figure 9:
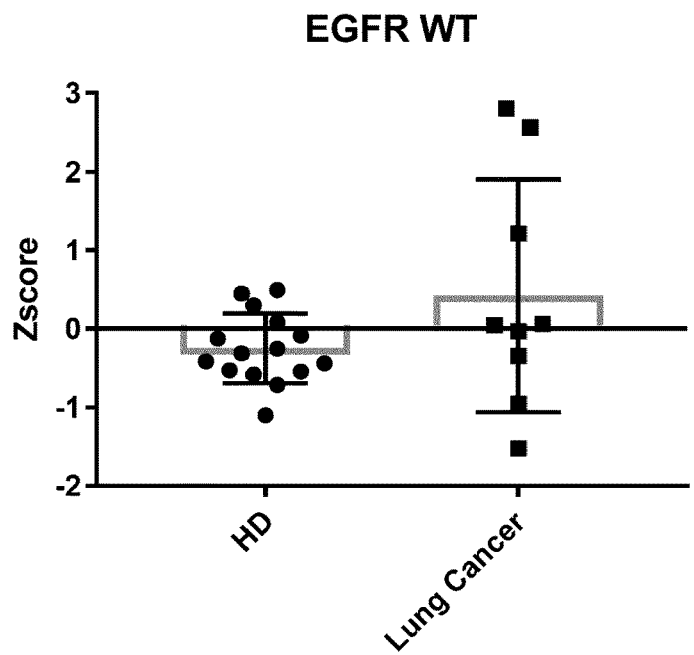
FIG. 9 depicts the score of EGFR levels as measured from exosomes isolated from the plasma of heatlhy or lung cancer patients by immunocapture with an anti CA-IX antibody.

FIG. 9 shows the results of a quantitative analysis of the EGFR wild type (WT) gene by real time PCR on DNA extracted from HD and lung cancer patients samples following exosome immunoisolation with anti-CAIX-antibody-coated beads. Zscore value of 0 was used as diagnostic threshold as previously described. 11 out of 15 (77%) HD plasma samples had negative Zscore and were considered as cancer negative while 5 out of 9 (60%) lung cancer plasma samples had positive Zscore and were considered as cancer positive. Overall, these data indicate that a diagnostic threshold for distinguishing healthy individuals from lung cancer patients can be generated using EGFR WT gene instead of BRAF WT gene as PCR readout.

Example 10

Diagnosis of Lung Cancer with HERV-W

Figure 10:
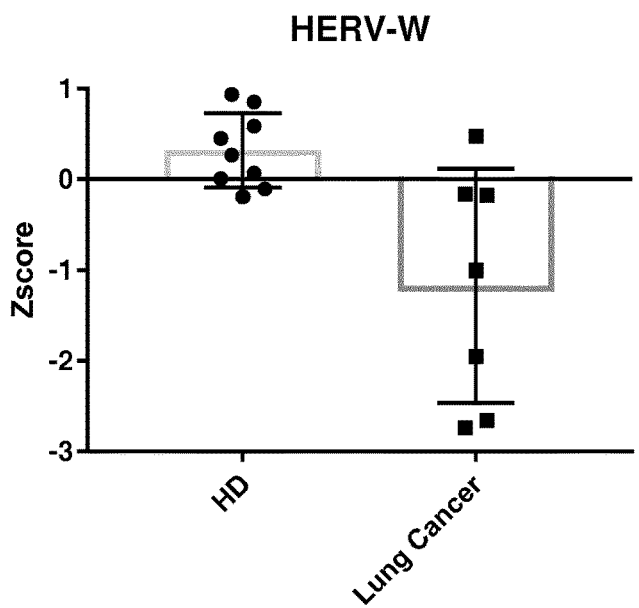
FIG. 10 depicts the score of HERV-W levels as measured from exosomes isolated from the plasma of heatlhy or lung cancer patients by immunocapture with an anti CA-IX antibody.

FIG. 10 shows the results of a quantitative analysis of the HERV-W retrotransposon element by real time PCR on DNA extracted from HD and lung cancer patient samples following exosome immunoisolation with anti-CAIX-antibody-coated beads. Zscore value of 0 was used as diagnostic threshold as previously described. 8 out of 10 (80%) HD plasma samples had positive Zscore and were considered as cancer negative while 6 out of 7 (85%) lung cancer plasma samples had negative Zscore and were considered as cancer positive. Overall, these data indicate that a diagnostic threshold for distinguishing healthy individuals from lung cancer patients can be generated using HERV-W retrotransposon element instead of BRAF WT gene as PCR readout.

Example 11

Diagnosis of Lung Cancer with LINE

Figure 11:
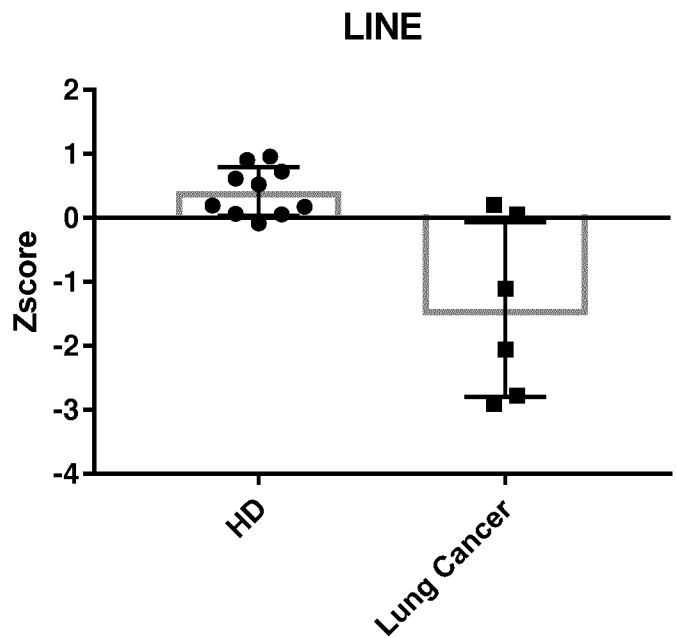
FIG. 11 depicts the score of LINE levels as measured from exosomes isolated from the plasma of heatlhy or lung cancer patients by immunocapture with an anti CA-IX antibody.

FIG. 11 shows the results of a quantitative analysis of the LINE retrotransposon element by real time PCR on DNA extracted from HD and lung cancer patient samples following exosome immunoisolation with anti-CAIX-antibody-coated beads. Zscore value of 0 was used as diagnostic threshold as previously described. 9 out of 10 (90%) HD plasma samples had positive Zscore and were considered as cancer negative while 4 out of 6 (67%) lung cancer plasma samples had negative Zscore and were considered as cancer positive. Overall, these data indicate that a diagnostic threshold for distinguishing healthy individuals from lung cancer patients can be generated using LINE retrotransposon element instead of BRAF WT gene as PCR readout.

Example 12

Diagnosis of Lung Cancer with c-Myc Gene

Figure 12:
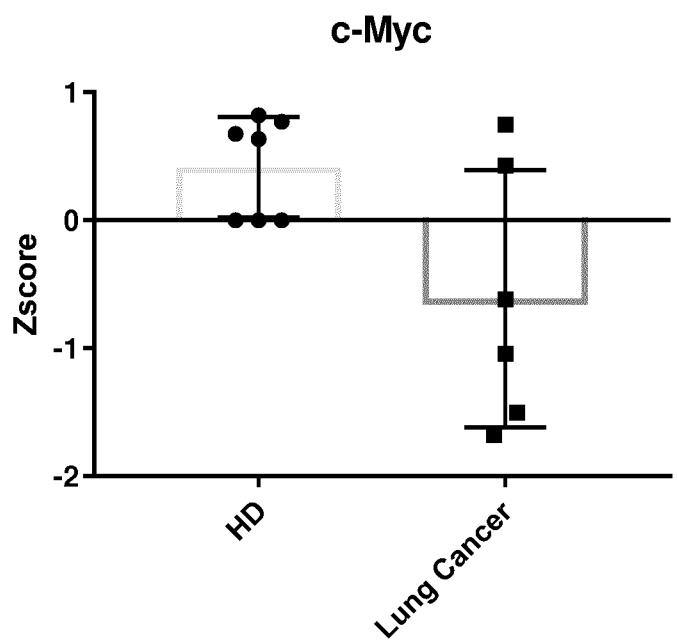
FIG. 12 depicts the score of c-Myc levels as measured from exosomes isolated from the plasma of heatlhy or lung cancer patients by immunocapture with an anti CA-IX antibody.

FIG. 12 shows the results of a quantitative analysis of the c-Myc gene by real time PCR on DNA extracted from HD and lung cancer patient samples following exosome immunoisolation with anti-CAIX-antibody-coated beads. Zscore value of 0 was used as diagnostic threshold as previously described. 7 out of 7 (100%) HD plasma samples had zero or positive Zscore and were considered as cancer negative while 4 out of 6 (67%) lung cancer plasma samples had negative Zscore and were considered as cancer positive. Overall, these data indicate that a diagnostic threshold for distinguishing healthy individuals from lung cancer patients can be generated using c-Myc gene instead of BRAF WT gene as PCR readout.

Example 13

Diagnosis of Breast Cancer with HERV-W

Figure 13:
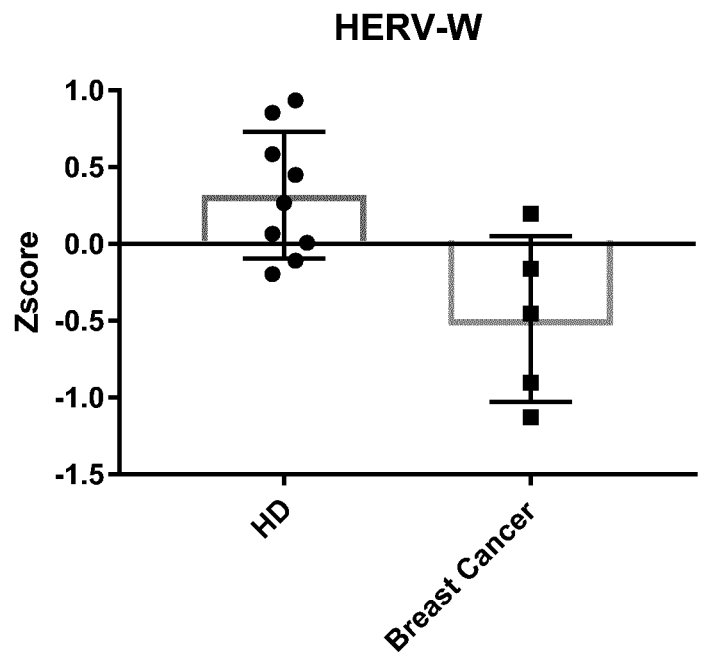
FIG. 13 depicts the score of HERV-W levels as measured from exosomes isolated from the plasma of heatlhy or breast cancer patients by immunocapture with an anti CA-IX antibody.

FIG. 13 shows the results of a quantitative analysis of the HERV-W retrotransposon element by real time PCR on DNA extracted from HD and breast cancer patient samples following exosome immunoisolation with anti-CAIX-antibody-coated beads. Zscore value of 0 was used as diagnostic threshold as previously described. 7 out of 9 (78%) HD plasma samples had positive Zscore and were considered as cancer negative while 4 out of 5 (80%) breast cancer plasma samples had negative Zscore and were considered as cancer positive. Overall, these data indicate that a diagnostic threshold for distinguishing healthy individuals from breast cancer patients can be generated using HERV-W retrotransposon element instead of BRAF WT gene as PCR readout.

Example 14

Diagnosis of Breast Cancer with LINE

Figure 14:
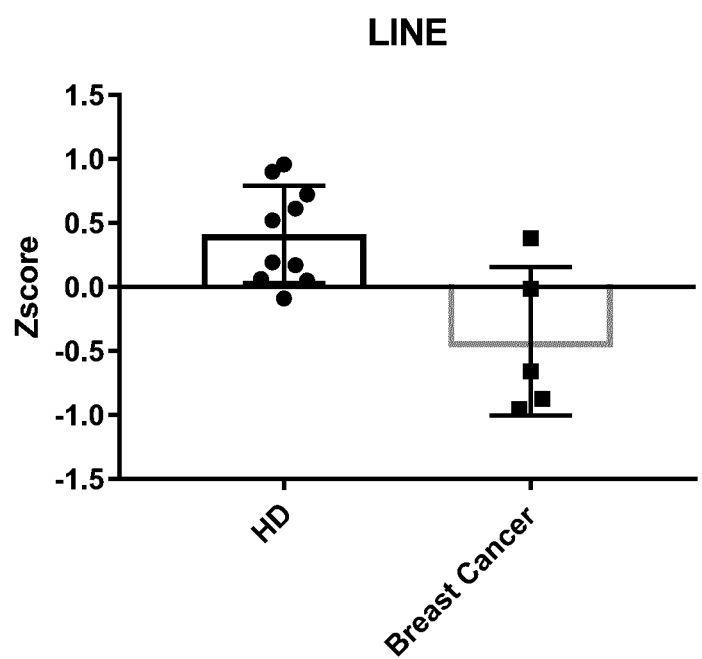
FIG. 14 depicts the score of LINE levels as measured from exosomes isolated from the plasma of heatlhy or breast cancer patients by immunocapture with an anti CA-IX antibody.

FIG. 14 shows the results of a quantitative analysis of the LINE retrotransposon element by real time PCR on DNA extracted from HD and breast cancer patient samples following exosome immunoisolation with anti-CAIX-antibody-coated beads. Zscore value of 0 was used as diagnostic threshold as previously described. 9 out of 10 (90%) HD plasma samples had positive Zscore and were considered as cancer negative while 4 out of 5 (80%) breast cancer plasma samples had negative Zscore and were considered as cancer positive. Overall, these data indicate that a diagnostic threshold for distinguishing healthy individuals from breast cancer patients can be generated using LINE retrotransposon element instead of BRAF WT gene as PCR readout.

Example 15

Diagnosis of Prostate Cancer with AR-WT

Figure 15:
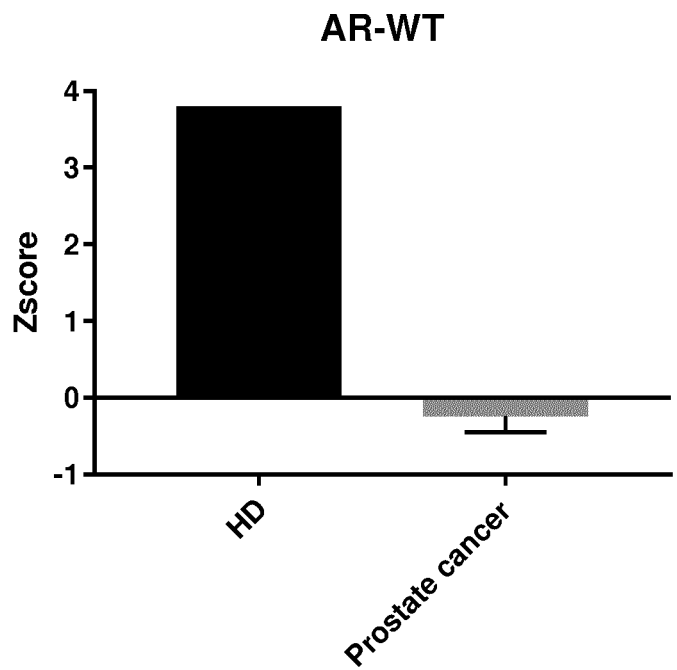
FIG. 15 depicts the score of AR-WT levels as measured from exosomes isolated from the plasma of heatlhy or prostate cancer patients by immunocapture with an anti CA-IX antibody.

FIG. 15 shows the results of a quantitative analysis of the AR WT gene by real time PCR on DNA extracted from HD and prostate cancer patient samples following exosome immunoisolation with anti-CAIX-antibody-coated beads. Zscore value of 0 was used as diagnostic threshold as previously described. 1 out of 1 (100%) HD plasma samples had positive Zscore and was considered as cancer negative while 15 out of 16 (93%) prostate cancer plasma samples had negative Zscore and were considered as cancer positive. Overall, these data indicate that a diagnostic threshold for distinguishing healthy individuals from prostate cancer patients can be generated using AR WT gene instead of BRAF WT gene as PCR readout.

Example 16

Diagnosis of Prostate Cancer with AR-T878A

Figure 16:
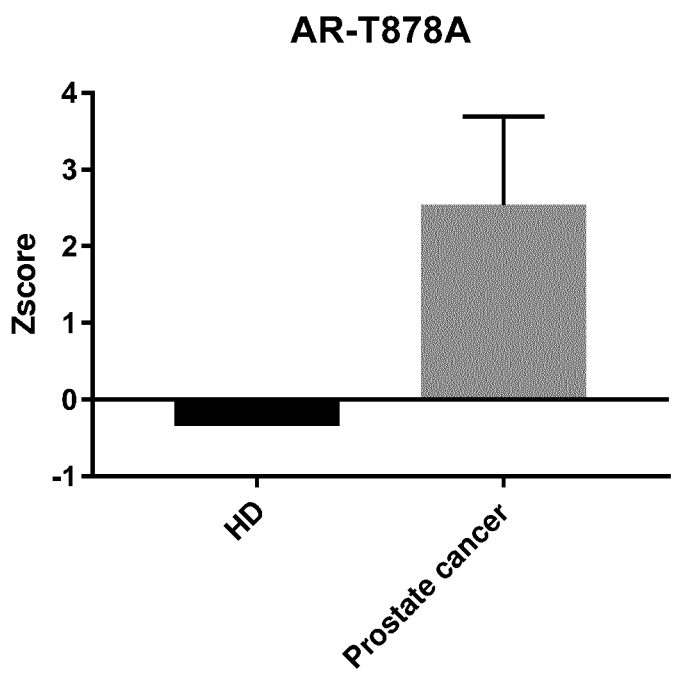
FIG. 16 depicts the score of AR-T878A levels as measured from exosomes isolated from the plasma of heatlhy or prostate cancer patients by immunocapture with an anti CA-IX antibody.

FIG. 16 shows the results of a quantitative analysis of the AR T878A gene by real time PCR on DNA extracted from HD and prostate cancer patient samples following exosome immunoisolation with anti-CAIX-antibody-coated beads. Zscore value of 0 was used as diagnostic threshold as previously described. 1 out of 1 (100%) HD plasma samples had positive Zscore and was considered as cancer negative while 2 out of 2 (100%) prostate cancer plasma samples had negative Zscore and were considered as cancer positive. Overall, these data indicate that a diagnostic threshold for distinguishing healthy individuals from prostate cancer patients can be generated using AR T878A gene instead of BRAF WT gene as PCR readout.

Example 17

Diagnosis of Colorectal Cancer with HERV-W

Figure 17:
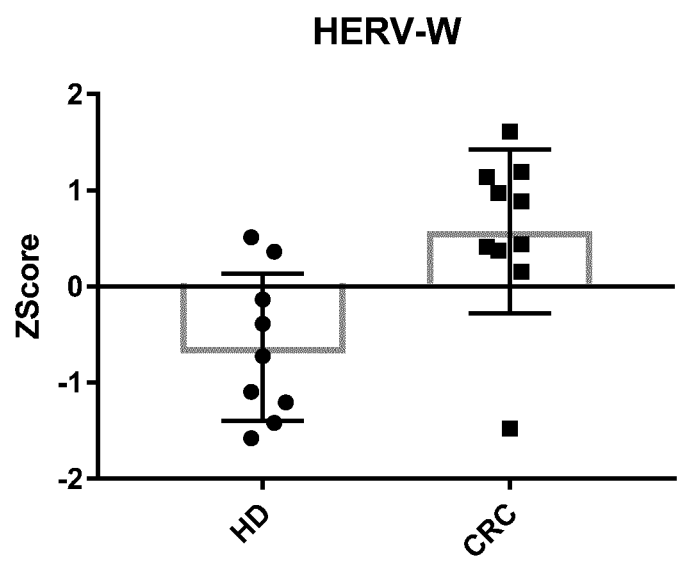
FIG. 17 depicts the score of HERV-W levels as measured from exosomes isolated from the plasma of heatlhy or colorectal cancer patients by immunocapture with an anti CA-IX antibody.

FIG. 17 shows the results of a quantitative analysis of the HERV-W retrotransposon element by real time PCR on DNA extracted from HD and colorectal (CRC) cancer patient samples following exosome immunoisolation with anti-CAIX-antibody-coated beads.

Zscore value of 0 was used as diagnostic threshold as previously described. 8 out of 10 (80%) HD plasma samples had negative Zscore and was considered as cancer negative while 9 out of 10 (90%) CRC plasma samples had positive Zscore and were considered as cancer positive. Overall, these data indicate that a diagnostic threshold for distinguishing healthy individuals from CRC patients can be generated using HERV-W retrotransposon element instead of BRAF WT gene as PCR readout.

Example 18

Diagnosis of Colorectal Cancer with LINE

Figure 18:
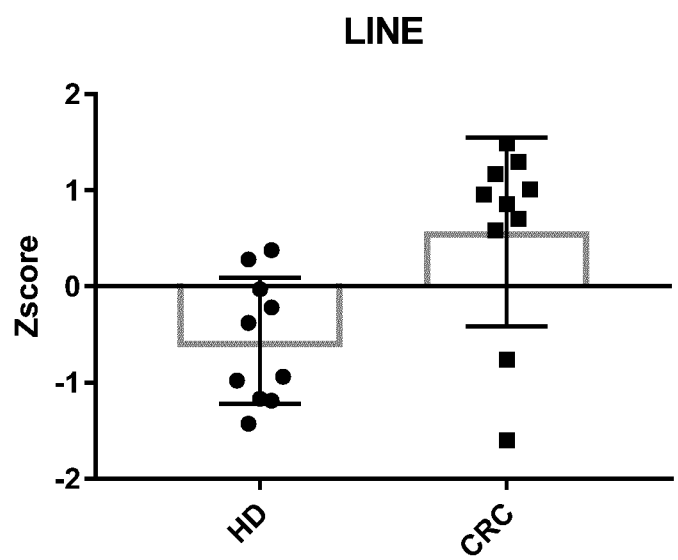
FIG. 18 depicts the score of LINE levels as measured from exosomes isolated from the plasma of heatlhy or colorectal cancer patients by immunocapture with an anti CA-IX antibody.

FIG. 18 shows the results of a quantitative analysis of the LINE retrotransposon element by real time PCR on DNA extracted from HD and colorectal (CRC) cancer patient samples following exosome immunoisolation with anti-CAIX-antibody-coated beads. Zscore value of 0 was used as diagnostic threshold as previously described. 7 out of 9 (77%) HD plasma samples had negative Zscore and was considered as cancer negative while 8 out of 10 (80%) CRC plasma samples had positive Zscore and were considered as cancer positive. Overall, these data indicate that a diagnostic threshold for distinguishing healthy individuals from CRC patients can be generated using LINE retrotransposon element instead of BRAF WT gene as PCR readout.

Example 19

Diagnosis of Gastric Cancer with HERV-W

Figure 19:
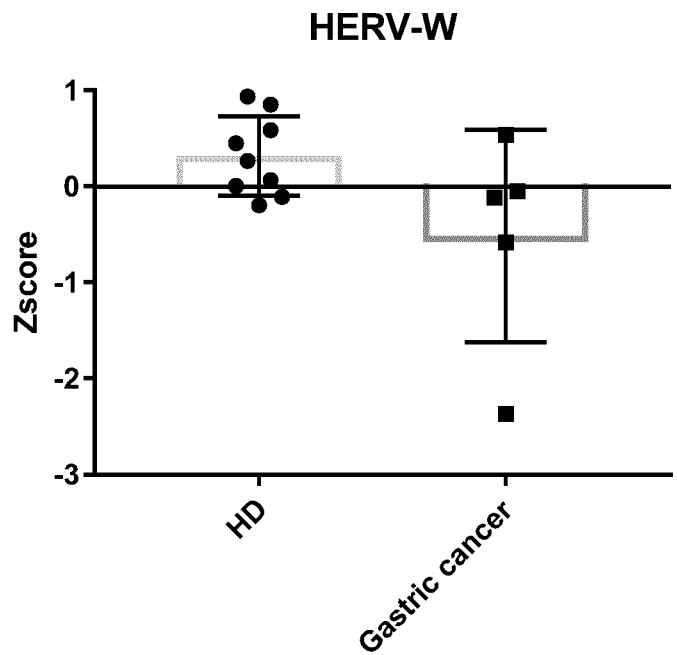
FIG. 19 depicts the score of HERV-W levels as measured from exosomes isolated from the plasma of heatlhy or gastric cancer patients by immunocapture with an anti CA-IX antibody.

FIG. 19 shows the results of a quantitative analysis of the HERV-W retrotransposon element by real time PCR on DNA extracted from HD and gastric cancer patient samples following exosome immunoisolation with anti-CAIX-antibody-coated beads. Zscore value of 0 was used as diagnostic threshold as previously described. 7 out of 10 (70%) HD plasma samples had positive Zscore and was considered as cancer negative while 4 out of 5 (80%) gastric plasma samples had negative Zscore and were considered as cancer positive. Overall, these data indicate that a diagnostic threshold for distinguishing healthy individuals from gastric patients can be generated using HERV-W retrotransposon element instead of BRAF WT gene as PCR readout.

Example 20

Diagnosis of Gastric Cancer with LINE

Figure 20:
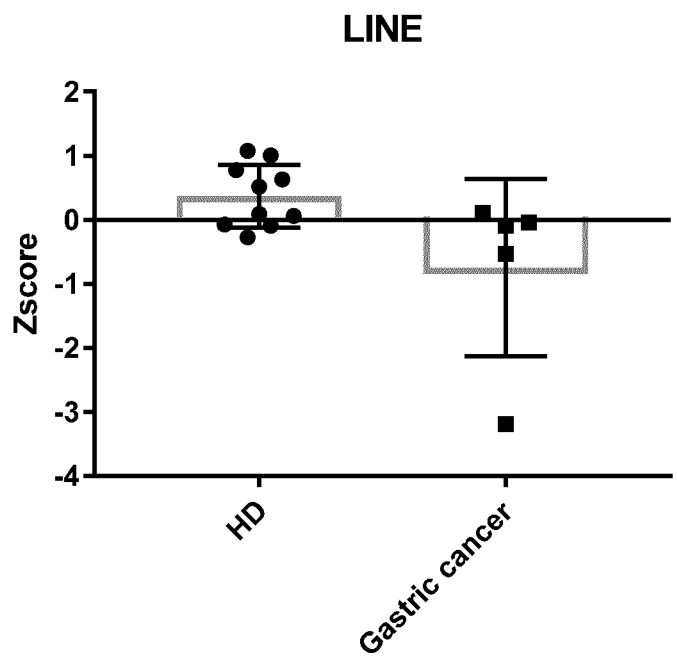
FIG. 20 depicts the score of LINE levels as measured from exosomes isolated from the plasma of heatlhy or gastric cancer patients by immunocapture with an anti CA-IX antibody.

FIG. 20 shows the results of a quantitative analysis of the LINE retrotransposon element by real time PCR on DNA extracted from HD and gastric cancer patient samples following exosome immunoisolation with anti-CAIX-antibody-coated beads. Zscore value of 0 was used as diagnostic threshold as previously described. 7 out of 10 (70%) HD plasma samples had positive Zscore and was considered as cancer negative while 4 out of 5 (80%) gastric plasma samples had negative Zscore and were considered as cancer positive. Overall, these data indicate that a diagnostic threshold for distinguishing healthy individuals from gastric patients can be generated using LINE retrotransposon element instead of BRAF WT gene as PCR readout.

Example 21

Diagnosis of Ovarian Cancer with c-Myc

Figure 21:
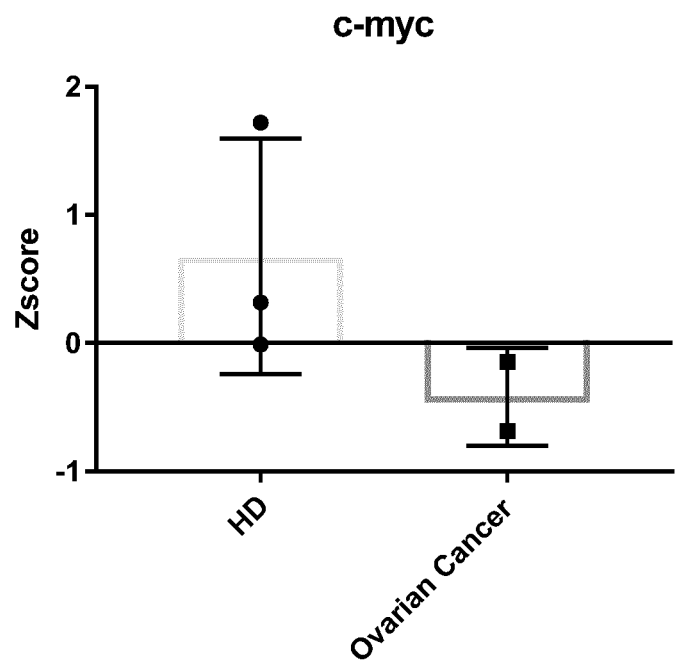
FIG. 21 depicts the score of c-Myc levels as measured from exosomes isolated from the plasma of heatlhy or ovarian cancer patients by immunocapture with an anti CA-IX antibody.

FIG. 21 shows the results of a quantitative analysis of the c-Myc gene by real time PCR on DNA extracted from HD and ovarian cancer patient samples following exosome immunoisolation with anti-CAIX-antibody-coated beads. Zscore value of 0 was used as diagnostic threshold as previously described. 2 out of 3 (70%) HD plasma samples had positive Zscore and was considered as cancer negative while 2 out of 2 (100%) ovarian plasma samples had negative Zscore and were considered as cancer positive. Overall, these data indicate that a diagnostic threshold for distinguishing healthy individuals from ovarian patients can be generated using c-Myc gene instead of BRAF WT gene as PCR readout.

Example 22

Diagnosis of Lung Cancer with HERV-W

Figure 22:
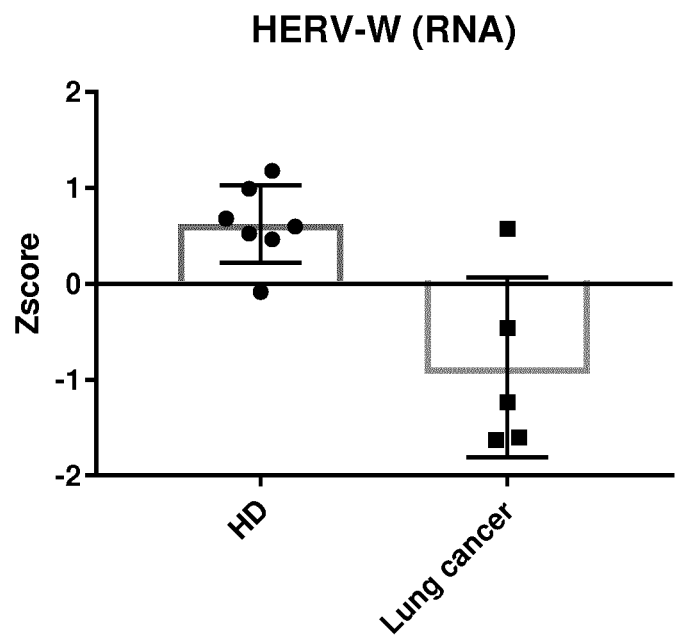
FIG. 22 depicts the score of HERV-W levels as measured from exosomes isolated from the plasma of heatlhy or lung cancer patients byimmunocapture with an anti CA-IX antibody.

FIG. 22 shows the results of a quantitative analysis of the HERV-W retrotransposon element by real time PCR on RNA extracted from HD and lung cancer patient samples following exosome immunoisolation with anti-CAIX-antibody-coated beads. Zscore value of 0 was used as diagnostic threshold as previously described. 6 out of 8 (77%) HD plasma samples had positive Zscore and were considered as cancer negative while 4 out of 5 (80%) lung cancer plasma samples had negative Zscore and were considered as cancer positive. Overall, these data indicate that a diagnostic threshold for distinguishing healthy individuals from lung cancer patients can be generated using HERV-W retrotransposon element from RNA instead of BRAF WT gene as PCR readout.

Example 23

Diagnosis of Lung Cancer with c-Myc

Figure 23:
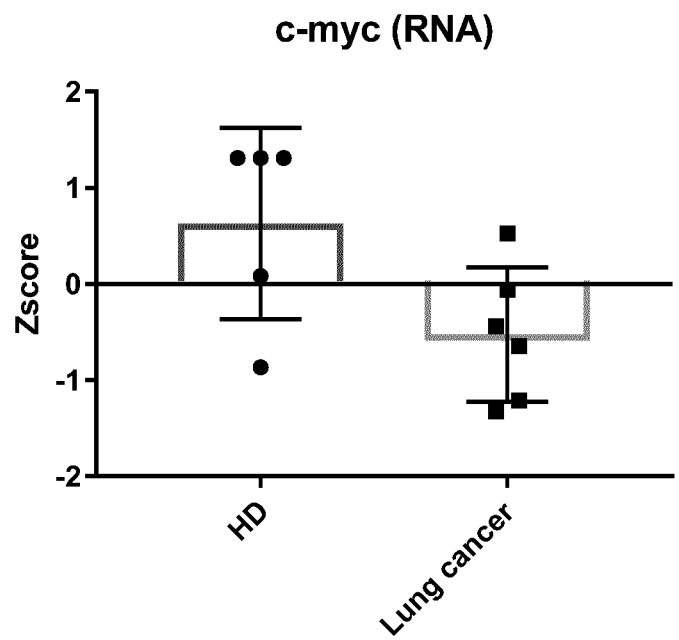
FIG. 23 depicts the score of c-Myc levels as measured from exosomes isolated from the plasma of heatlhy or lung cancer patients by immunocapture with an anti CA-IX antibody.

FIG. 23 shows the results of a quantitative analysis of the c-Myc messenger RNA (mRNA) by real time PCR on RNA extracted from HD and lung cancer patient samples following exosome immunoisolation with anti-CAIX-antibody-coated beads. Zscore value of 0 was used as diagnostic threshold as previously described. 4 out of 5 (80%) HD plasma samples had positive Zscore and were considered as cancer negative while 5 out of 6 (85%) lung cancer plasma samples had negative Zscore and were considered as cancer positive. Overall, these data indicate that a diagnostic threshold for distinguishing healthy individuals from lung cancer patients can be generated using c-Myc mRNA instead of BRAF WT gene as PCR readout.

Example 24

Diagnosis of Lung Cancer with LINE

Figure 24:
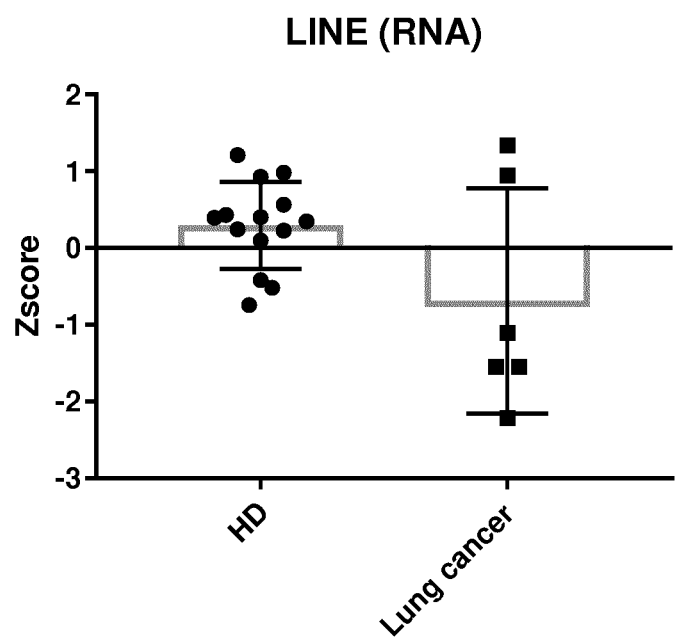
FIG. 24 depicts the score of LINE levels as measured from exosomes isolated from the plasma of heatlhy or lung cancer patients by immunocapture with an anti CA-IX antibody.

FIG. 24 shows the results of a quantitative analysis of the LINE retrotransposon element by real time PCR on RNA extracted from HD and lung cancer patient samples following exosome immunoisolation with anti-CAIX-antibody-coated beads. Zscore value of 0 was used as diagnostic threshold as previously described. 12 out of 15 (80%) HD plasma samples had positive Zscore and were considered as cancer negative while 4 out of 6 (67%) lung cancer plasma samples had negative Zscore and were considered as cancer positive. Overall, these data indicate that a diagnostic threshold for distinguishing healthy individuals from lung cancer patients can be generated using LINE retrotransposon element from RNA instead of BRAF WT gene as PCR readout.

Example 25

Diagnosis of Colorectal Cancer with LINE

Figure 25:
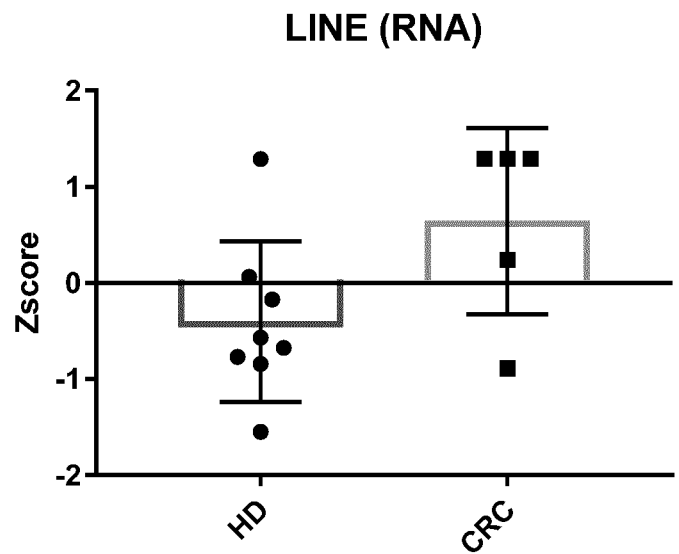
FIG. 25 depicts the score of LINE levels as measured from exosomes isolated from the plasma of heatlhy or colorectal cancer patients by immunocapture with an anti CA-IX antibody.

FIG. 25 shows the results of a quantitative analysis of the LINE retrotransposon element by real time PCR on RNA extracted from HD and colorectal cancer patient (CRC) samples following exosome immunoisolation with anti-CAIX-antibody-coated beads. Zscore value of 0 was used as diagnostic threshold as previously described. 7 out of 9 (77%) HD plasma samples had negative Zscore and were considered as cancer negative while 4 out of 5 (80%) CRC plasma samples had positive Zscore and were considered as cancer positive. Overall, these data indicate that a diagnostic threshold for distinguishing healthy individuals from CRC patients can be generated using LINE retrotransposon element from RNA instead of BRAF WT gene as PCR readout.

Example 26

Diagnosis of Colorectal Cancer with EGFR

Figure 26:
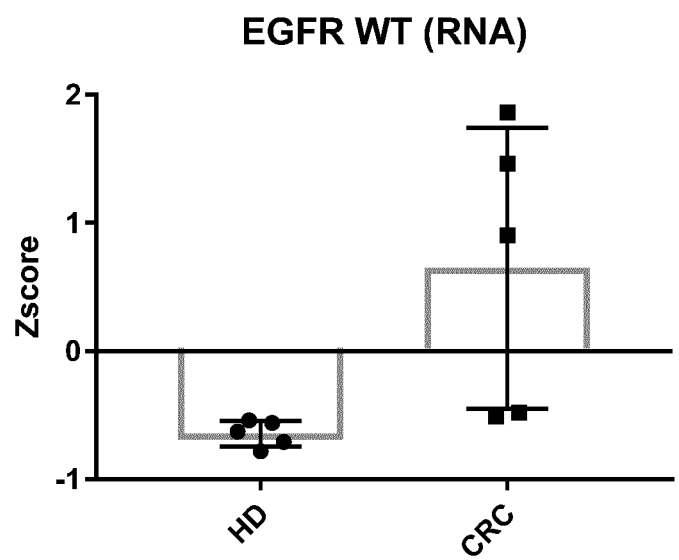
FIG. 26 depicts the score of EGFR levels as measured from exosomes isolated from the plasma of heatlhy or colorectal cancer patients by immunocapture with an anti CA-IX antibody.

FIG. 26 shows the results of a quantitative analysis of the EGFR WT messenger RNA (mRNA) by real time PCR on RNA extracted from HD and colorectal cancer patient (CRC) samples following exosome immunoisolation with anti-CAIX-antibody-coated beads. Zscore value of 0 was used as diagnostic threshold as previously described. 5 out of 5 (100%) HD plasma samples had negative Zscore and were considered as cancer negative while 3 out of 5 (60%) CRC plasma samples had positive Zscore and were considered as cancer positive. Overall, these data indicate that a diagnostic threshold for distinguishing healthy individuals from CRC patients can be generated using EGFR WT mRNA instead of BRAF WT gene as PCR readout.

Example 27

Diagnosis of Colorectal Cancer with HERV-W

Figure 27:
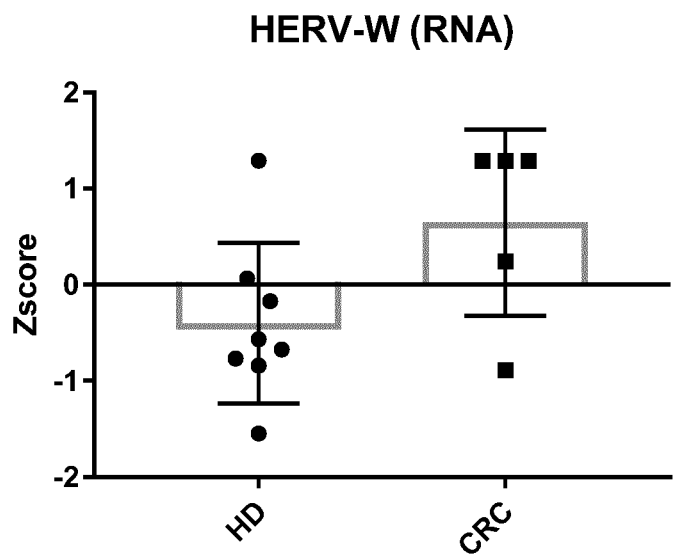
FIG. 27 depicts the score of HERV-W levels as measured from exosomes isolated from the plasma of heatlhy or colorectal cancer patients by immunocapture with an anti CA-IX antibody.

FIG. 27 shows the results of a quantitative analysis of the HERV-W retrotransposon element by real time PCR on RNA extracted from HD and colorectal cancer patient (CRC) samples following exosome immunoisolation with anti-CAIX-antibody-coated beads. Zscore value of 0 was used as diagnostic threshold as previously described. 6 out of 8 (75%) HD plasma samples had negative Zscore and were considered as cancer negative while 4 out of 5 (80%) CRC plasma samples had positive Zscore and were considered as cancer positive. Overall, these data indicate that a diagnostic threshold for distinguishing healthy individuals from CRC patients can be generated using HERV-W retrotransposon on RNA instead of BRAF WT gene as PCR readout.

Example 28

Diagnosis of Breast Cancer with LINE

Figure 28:
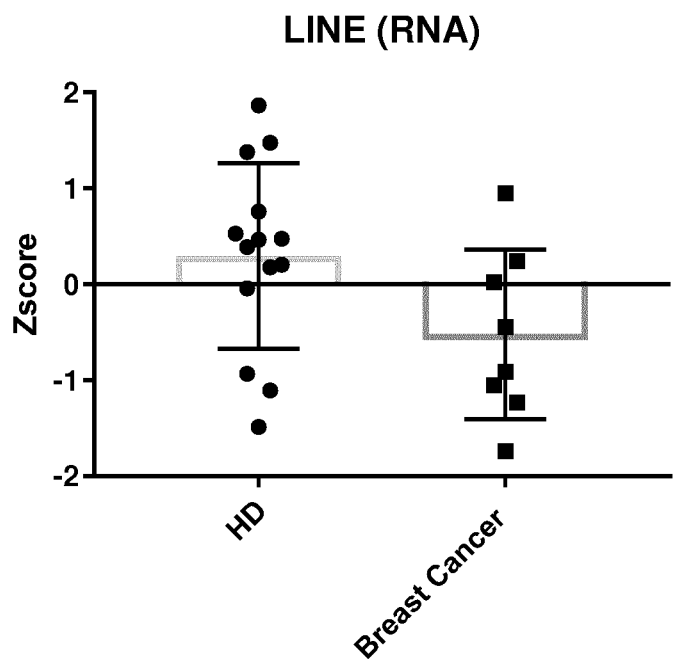
FIG. 28 depicts the score of LINE levels as measured from exosomes isolated from the plasma of heatlhy or breast cancer patients by immunocapture with an anti CA-IX antibody.

FIG. 28 shows the results of a quantitative analysis of the LINE retrotransposon element by real time PCR on RNA extracted from HD and breast cancer patient samples following exosome immunoisolation with anti-CAIX-antibody-coated beads. Zscore value of 0 was used as diagnostic threshold as previously described. 12 out of 15 (80%) HD plasma samples had positive Zscore and were considered as cancer negative while 5 out of 8 (62%) breast cancer plasma samples had negative Zscore and were considered as cancer positive. Overall, these data indicate that a diagnostic threshold for distinguishing healthy individuals from breast cancer patients can be generated using LINE retrotransposon element from RNA instead of BRAF WT gene as PCR readout.

Example 29

Diagnosis of Melanoma with HERV-W

Figure 29:
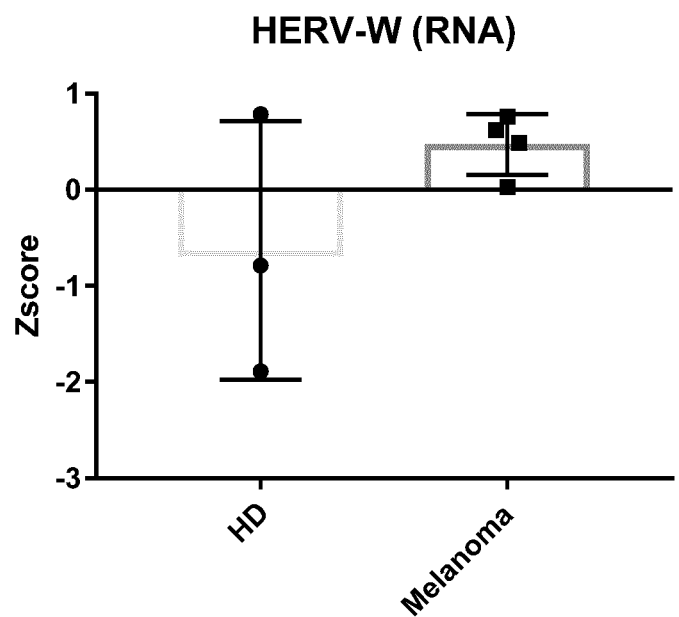
FIG. 29 depicts the score of HERV-W levels as measured from exosomes isolated from the plasma of heatlhy or melanoma patients by immunocapture with an anti CA-IX antibody.

FIG. 29 shows the results of a quantitative analysis of the HERV-W retrotransposon element by real time PCR on RNA extracted from HD and melanoma patient samples following exosome immunoisolation with anti-CAIX-antibody-coated beads. Zscore value of 0 was used as diagnostic threshold as previously described. 2 out of 3 (66%) HD plasma samples had Zscore negative and were considered as cancer negative while 4 out of 4 (100%) melanoma plasma samples had positive Zscore and were considered as cancer positive. Overall, these data indicate that a diagnostic threshold for distinguishing healthy individuals from melanoma patients can be generated using HERV-W retrotransposon element from RNA instead of BRAF WT gene as PCR readout.

Example 30

Diagnosis of Ovarian Cancer with HERV-W

Figure 30:
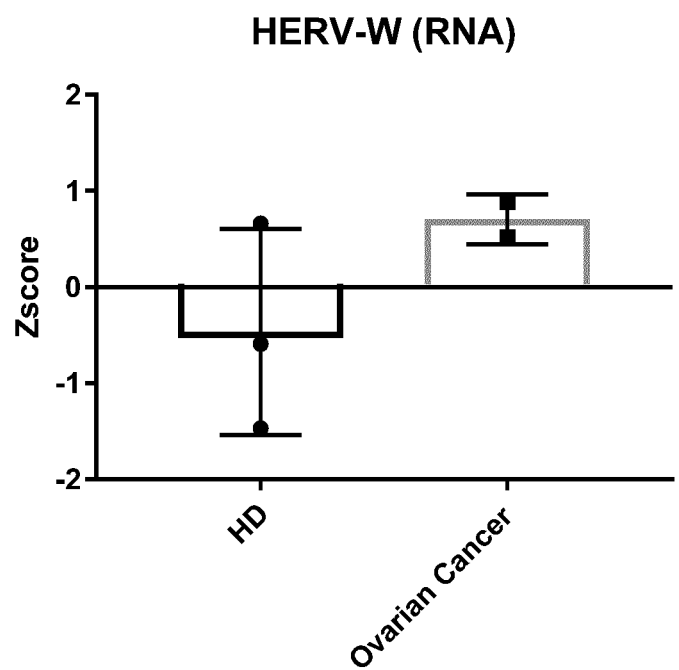
FIG. 30 depicts the score of HERV-W levels as measured from exosomes isolated from the plasma of heatlhy or ovarian cancer patients by immunocapture with an anti CA-IX antibody.

FIG. 30 shows the results of a quantitative analysis of the HERV-W retrotransposon element by real time PCR on RNA extracted from HD and ovarian cancer patient samples following exosome immunoisolation with anti-CAIX-antibody-coated beads. Zscore value of 0 was used as diagnostic threshold as previously described. 2 out of 3 (66%) HD plasma samples had Zscore negative and were considered as cancer negative while 2 out of 2 (100%) ovarian cancer plasma samples had positive Zscore and were considered as cancer positive. Overall, these data indicate that a diagnostic threshold for distinguishing healthy individuals from ovarian cancer patients can be generated using HERV-W retrotransposon element from RNA instead of BRAF WT gene as PCR readout.

Example 31

Diagnosis of Prostate Cancer with AR-WT

Figure 31:
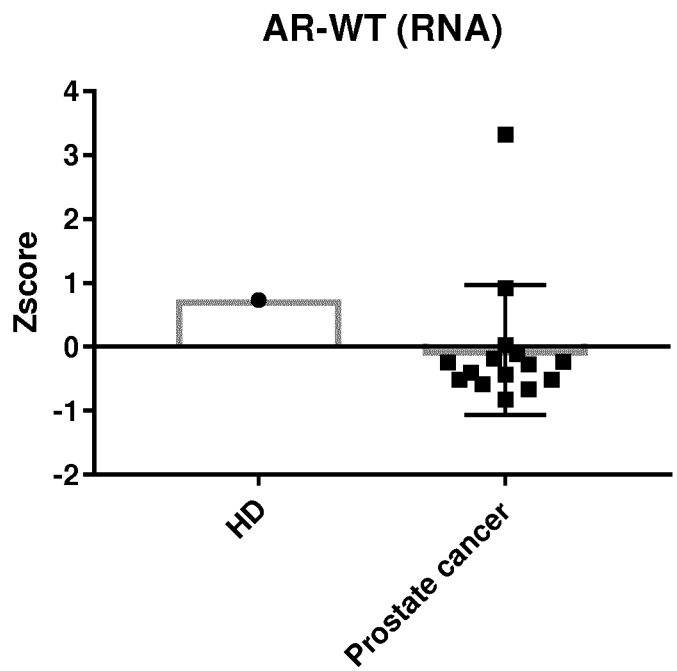
FIG. 31 depicts the score of AR-WT levels as measured from exosomes isolated from the plasma of heatlhy or prostate cancer patients by immunocapture with an anti CA-IX antibody.

FIG. 31 shows the results of a quantitative analysis of the androgen receptor (AR)-WT gene by real time PCR on RNA extracted from HD and prostate cancer patient samples following exosome immunoisolation with anti-CAIX-antibody-coated beads. Zscore value of 0 was used as diagnostic threshold as previously described. 1 out of 1 (100%) HD plasma samples had Zscore positive and were considered as cancer negative while 12 out of 15 (80%) prostate cancer plasma samples had negative Zscore and were considered as cancer positive. Overall, these data indicate that a diagnostic threshold for distinguishing healthy individuals from prostate cancer patients can be generated using AR-WT gene from RNA instead of BRAF WT gene as PCR readout.

Example 32

Diagnosis of Prostate Cancer with AR-V7

Figure 32:
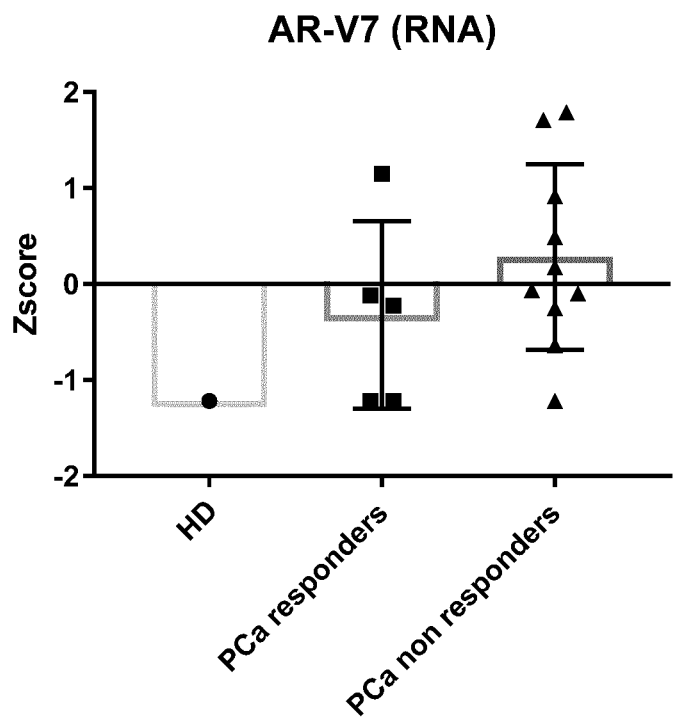
FIG. 32 depicts the score of AR-V7 levels as measured from exosomes isolated from the plasma of heatlhy or prostate cancer patients by immunocapture with an anti CA-IX antibody.

FIG. 32 shows the results of a quantitative analysis of the androgen receptor splicing variant 7 (AR-V7) gene by real time PCR on RNA extracted from HD and prostate cancer patient samples following exosome immunoisolation with anti-CAIX-antibody-coated beads. Zscore value of 0 was used as diagnostic threshold as previously described. 1 out of 1 (100%) HD plasma samples had Zscore positive and were considered as cancer negative. 4 out of 6 (67%) prostate cancer patients responding to AR-inhibitors had negative Zscore and were considered true responders while 5 out of 10 (50%) prostate cancer plasma samples non responding to AR-inhibitors had positive Zscore and were considered as true non responders. Overall, these data indicate that a diagnostic threshold for distinguishing healthy individuals and responder prostate cancer patients from non responder cancer patients can be generated using AR-V7 gene from RNA.

Example 33

Diagnosis of Bladder Cancer with LINE

Figure 33:
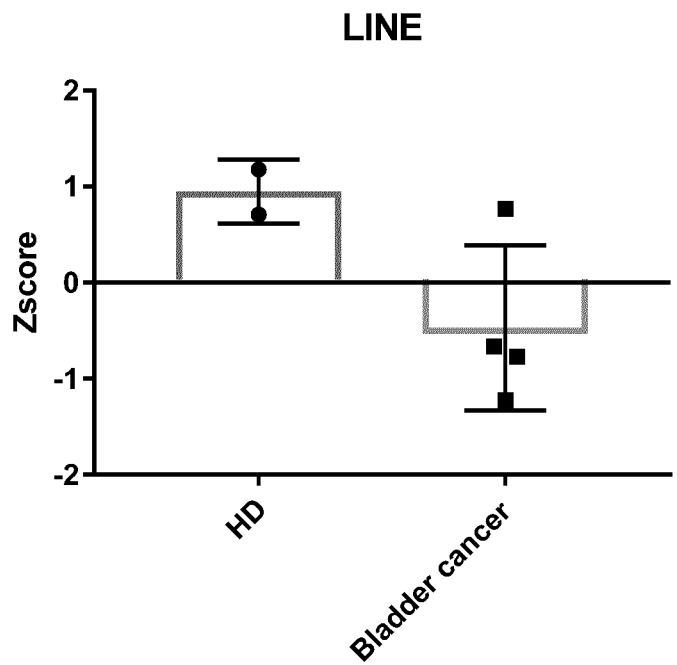
FIG. 33 depicts the score of LINE levels as measured from exosomes isolated from the urine of heatlhy or bladder cancer patients by immunocapture with an anti CA-IX antibody.

FIG. 33 shows the results of a quantitative analysis of the LINE retrotransposon element by real time PCR on DNA extracted from HD and bladder cancer patient samples following exosome immunoisolation with anti-CAIX-antibody-coated beads. Zscore value of 0 was used as diagnostic threshold as previously described. 2 out of 2 (100%) HD urine samples had positive Zscore and were considered as cancer negative while 3 out of 4 (75%) bladder cancer urine samples had negative Zscore and were considered as cancer positive. Overall, these data indicate that a diagnostic threshold for distinguishing healthy individuals from bladder cancer patients can be generated using LINE retrotransposon element.

Example 34

Diagnosis of Bladder Cancer with HERV-W

Figure 34:
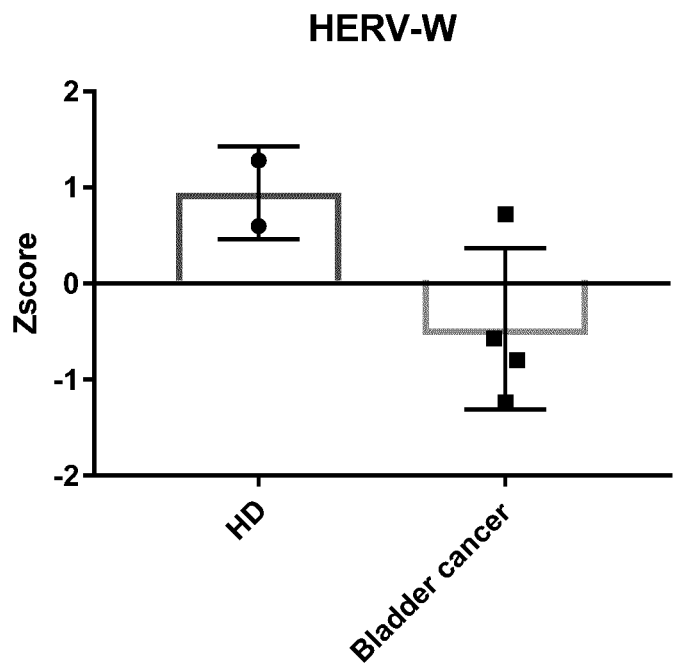
FIG. 34 depicts the score of HERV-W levels as measured from exosomes isolated from the urine of heatlhy or bladder cancer patients by immunocapture with an anti CA-IX antibody.

FIG. 34 shows the results of a quantitative analysis of the HERV-W retrotransposon element by real time PCR on DNA extracted from HD and bladder cancer patient samples following exosome immunoisolation with anti-CAIX-antibody-coated beads. Zscore value of 0 was used as diagnostic threshold as previously described. 2 out of 2 (100%) HD urine samples had positive Zscore and were considered as cancer negative while 3 out of 4 (75%) bladder cancer urine samples had negative Zscore and were considered as cancer positive. Overall, these data indicate that a diagnostic threshold for distinguishing healthy individuals from bladder cancer patients can be generated using HERV-W retrotransposon element.

Example 35

Diagnosis of Bladder Cancer with c-Myc

Figure 35:
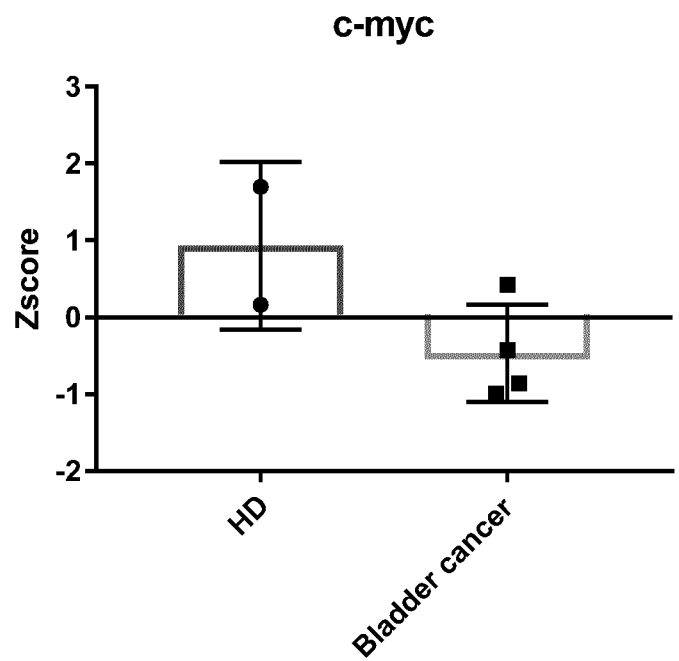
FIG. 35 depicts the score of c-Myc levels as measured from exosomes isolated from the urine of heatlhy or bladder cancer patients by immunocapture with an anti CA-IX antibody.

FIG. 35 shows the results of a quantitative analysis of the c-Myc gene by real time PCR on DNA extracted from HD and bladder cancer patient samples following exosome immunoisolation with anti-CAIX-antibody-coated beads. Zscore value of 0 was used as diagnostic threshold as previously described. 2 out of 2 (100%) HD urine samples had positive Zscore and were considered as cancer negative while 3 out of 4 (75%) bladder cancer urine samples had negative Zscore and were considered as cancer positive. Overall, these data indicate that a diagnostic threshold for distinguishing healthy individuals from bladder cancer patients can be generated using c-Myc gene.

Example 36

Diagnosis of Bladder Cancer with LINE

Figure 36:
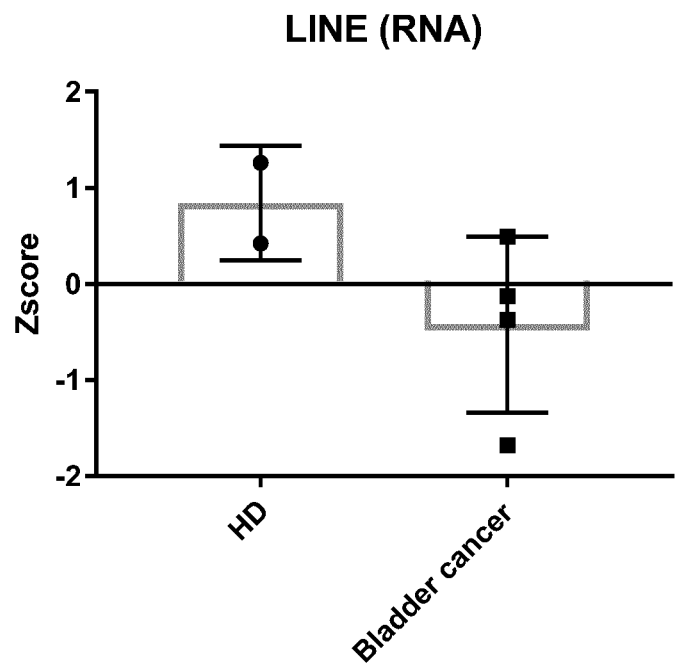
FIG. 36 depicts the score of LINE levels as measured from exosomes isolated from the urine of heatlhy or bladder cancer patients by immunocapture with an anti CA-IX antibody.

FIG. 36 shows the results of a quantitative analysis of the LINE retrotransposon element RNA by real time PCR from HD and bladder cancer patient samples following exosome immunoisolation with anti-CAIX-antibody-coated beads. Zscore value of 0 was used as diagnostic threshold as previously described. 2 out of 2 (100%) HD urine samples had positive Zscore and were considered as cancer negative while 3 out of 4 (75%) bladder cancer urine samples had negative Zscore and were considered as cancer positive. Overall, these data indicate that a diagnostic threshold for distinguishing healthy individuals from bladder cancer patients can be generated using the LINE retrotransposon element.

BIBLIOGRAPHY

1) Chamie K, Klopfer P, Bevan P, Storkel S, Said J, Fall B, Belldegrun A S, Pantuck A J. Carbonic anhydrase-IX score is a novel biomarker that predicts recurrence and survival for high-risk, nonmetastatic renal cell carcinoma: Data from the phase III ARISER clinical trial. Urol Oncol. 2015 May; 33(5):204.

2) Pastorek J, Pastorekova S. Hypoxia-induced carbonic anhydrase IX as a target for cancer therapy: from biology to clinical use. Semin Cancer Biol. 2015 April; 31:52-64.

3) Takacova M, Bartosova M, Skvarkova L, Zatovicova M, Vidlickova I, Csaderova L, Barathova M, Breza J Jr, Bujdak P, Pastorek J, Breza J Sr, Pastorekova S. Carbonic anhydrase IX is a clinically significant tissue and serum biomarker associated with renal cell carcinoma. Oncol Lett. 2013 January; 5(1):191-197. Mutations of the BRAF gene in human cancer.

4) Davies H, Bignell G R, Cox C, Stephens P, Edkins S, Clegg S, Teague J, Woffendin H, Garnett M J, Bottomley W, Davis N, Dicks E, Ewing R, Floyd Y, Gray K, Hall S, Hawes R, Hughes J, Kosmidou V, Menzies A, Mould C, Parker A, Stevens C, Watt S, Hooper S, Wilson R, Jayatilake H, Gusterson B A, Cooper C, Shipley J, Hargrave D, Pritchard-Jones K, Maitland N, Chenevix-Trench G, Riggins G J, Bigner D D, Palmieri G, Cossu A, Flanagan A, Nicholson A, Ho J W, Leung S Y, Yuen S T, Weber B L, Seigler H F, Darrow T L, Paterson H, Marais R, Marshall C J, Wooster R, Stratton M R, Futreal P A. Mutation of the BRAF gene in human cancer. Nature. 2002 Jun. 27; 417(6892):949-54.

5) Corcoran R B, Dias-Santagata D, Bergethon K, Iafrate A J, Settleman J, Engelman J A BRAF gene amplification can promote acquired resistance to MEK inhibitors in cancer cells harboring the BRAF V600E mutation. Sci Signal. 2010 Nov. 23; 3(149):ra84.

6) Perincheri S, Hui P. KRAS mutation testing in clinical practice. Expert Rev Mol Diagn. 2015 March; 15(3):375-84.

7) Cercek A, Braghiroli M I, Chou J F, Hechtman J F, Kemeny N E, Saltz L, Capanu M, Yaeger R Clinical features and outcomes of patients with colorectal cancers harboring NRAS mutations. Clin Cancer Res. 2017 Apr. 26. 164.

8) Mandalà M, Merelli B, Massi D. Nras in melanoma: targeting the undruggable target. Crit Rev Oncol Hematol. 2014 November; 92(2):107-22.

9) Passaro A, Guerini-Rocco E, Pochesci A, Vacirca D, Spitaleri G, Catania C M, Rappa A, Barberis M, de Marinis F. Targeting EGFR T790M mutation in NSCLC: From biology to evaluation and treatment Pharmacol Res. 2017 March; 117:406-415.

10) Fang S, Wang Z. EGFR mutations as a prognostic and predictive marker in non-small-cell lung cancer. Drug Des Devel Ther. 2014 Sep. 26; 8:1595-611.

11) Gabay M, Li Y, Felsher D W. MYC activation is a hallmark of cancer initiation and maintenance. Cold Spring Harb Perspect Med. 2014 Jun. 2; 4(6).

12) Balaj L, Lessard R, Dai L, Cho Y J, Pomeroy S L, Breakefield X O, Skog J. Tumour microvesicles contain retrotransposon elements and amplified oncogene sequences. Nat Commun. 2011 Feb. 1; 2:180.

13) Romanel A, Gasi Tandefelt D, Conteduca V, Jayaram A, Casiraghi N, Wetterskog D, Salvi S, Amadori D, Zafeiriou Z, Rescigno P, Bianchini D, Gurioli G, Casadio V, Carreira S, Goodall J, Wingate A, Ferraldeschi R, Tunariu N, Flohr P, De Giorgi U, de Bono J S, Demichelis F, Attard G. Plasma AR and abiraterone-resistant prostate cancer. Sci Transl Med. 2015 Nov. 4; 7(312):312re10.

14) Antonarakis E S, Lu C, Wang H, Luber B, Nakazawa M, Roeser J C, Chen Y, Mohammad T A, Chen Y, Fedor H L, Lotan T L, Zheng Q, De Marzo A M, Isaacs J T, Isaacs W B, Nadal R, Paller C J, Denmeade S R, Carducci M A, Eisenberger M A, Luo J. AR-V7 and resistance to enzalutamide and abiraterone in prostate cancer. N Engl J Med. 2014 Sep. 11; 371(11):1028-38.

15) Cheadle C, Vawter M P, Freed W J, Becker KG. J Mol Diagn. 2003 May; 5(2):73-81.

16) Dorai Y, The Jounral of Urologyu, (2010), 183(4) supplement, e145, abstract 366.

The invention claimed is:

1. A method for in vitro quantification of a tumour-related nucleic acid sequence present in exosomes from a biological fluid, the method comprising:
   a) capturing exosomes from a sample of said biological fluid with an anti CA-IX antibody, wherein the sample comprises exosomes having a detectable level of a tumour-related nucleic acid sequence; and
   b) detecting a level of the tumour-related nucleic acid sequence present in the exosomes captured in step a) for in vitro quantification of the tumour-related nucleic acid sequence from said biological fluid, wherein the tumour-related nucleic acid sequence comprises a gene sequence from a target gene selected from the group consisting of: a BRAF gene, a KRAS gene, a HERV gene, a LINE gene, a c-Myc gene and an AR gene.

2. The method of claim 1, wherein the exosomes are derived from a tumour selected from the group consisting of: lung cancer, breast cancer, bladder cancer, renal cancer, prostate cancer, colorectal cancer, gastric cancer, ovarian cancer and melanoma.

3. The method of claim 1, wherein the tumour-related nucleic acid sequence is a wild-type sequence from the target gene.

4. The method of claim 1, wherein the tumour-related nucleic acid sequence is a mutated sequence from the target gene.

5. The method of claim 4, wherein the mutated sequence is selected from the group consisting of: an amplification, a point mutation, a deletion and an insertion.

6. The method of claim 1, wherein the biological fluid is selected from the group consisting of: blood, plasma, serum, urine and saliva.

* * * * *